US012064372B2

(12) United States Patent
Godinez et al.

(10) Patent No.: US 12,064,372 B2
(45) Date of Patent: Aug. 20, 2024

(54) FEMALE EXTERNAL URINARY DEVICE AND ASSEMBLY

(71) Applicant: Medline Industries, LP, Northfield, IL (US)

(72) Inventors: Saul Godinez, Chicago, IL (US); David S. Noskowicz, Spring Grove, IL (US); Sarah Dickinson, Glen Ellyn, IL (US); Becca Covode, Chicago, IL (US)

(73) Assignee: Medline Industries, LP, Northfield, IL (US)

( * ) Notice: Subject to any disclaimer, the term of this patent is extended or adjusted under 35 U.S.C. 154(b) by 518 days.

(21) Appl. No.: 16/535,590

(22) Filed: Aug. 8, 2019

(65) Prior Publication Data

US 2020/0046544 A1 Feb. 13, 2020

Related U.S. Application Data

(60) Provisional application No. 62/716,543, filed on Aug. 9, 2018.

(51) Int. Cl.
*A61F 5/455* (2006.01)
*A61B 10/00* (2006.01)
(Continued)

(52) U.S. Cl.
CPC ............ *A61F 5/455* (2013.01); *A61B 10/007* (2013.01); *A61F 5/4408* (2013.01); *A61F 5/451* (2013.01); *A61F 5/48* (2013.01); *A61G 9/006* (2013.01)

(58) Field of Classification Search
CPC .. A61F 5/4408; A61F 5/48; A61F 5/451–455; A61B 10/007; A61G 9/006
See application file for complete search history.

(56) References Cited

U.S. PATENT DOCUMENTS 1,742,080 A 12/1929 Jones
3,194,238 A 7/1965 Breece, Jr.
(Continued)

FOREIGN PATENT DOCUMENTS

EP 0613355 9/1994
JP 11113946 4/1999
(Continued)

OTHER PUBLICATIONS

International Search Report and Written Opinion for International Application No. PCT/US2019/045720 dated Nov. 19, 2019.
(Continued)

*Primary Examiner* — Susan S Su
*Assistant Examiner* — Ted Yang
(74) *Attorney, Agent, or Firm* — Fitch, Even, Tabin & Flannery LLP

(57) ABSTRACT

A female external urinary device useful in managing urine output of a female, such as for surgical use, includes a core having a suction channel and an interior reservoir fluidically communicating with the suction channel, an absorbent layer, and a fabric cover. Desirably, the urinary device includes a moderately absorbent soaker layer disposed inwardly with respect to the core. A urinary device assembly includes the core and a pelvic belt that may be secure to the core and positioned to collect urine from a female patient.

16 Claims, 23 Drawing Sheets

(51) Int. Cl.
  A61F 5/44      (2006.01)
  A61F 5/451     (2006.01)
  A61F 5/48      (2006.01)
  A61G 9/00      (2006.01)

(56)            References Cited

U.S. PATENT DOCUMENTS

| | | | |
|---|---|---|---|
| 3,349,768 A | 10/1967 | Keane | |
| 3,374,790 A | 3/1968 | Mayhorne | |
| 3,528,423 A | 9/1970 | Lee | |
| 3,995,329 A | 12/1976 | Williams | |
| 4,194,508 A | 3/1980 | Anderson | |
| 4,198,979 A | 4/1980 | Cooney | |
| 4,202,058 A | 5/1980 | Anderson | |
| 4,233,978 A | 11/1980 | Hickey | |
| 4,270,539 A | 6/1981 | Frosch | |
| 4,360,015 A | 11/1982 | Mayer | |
| 4,421,511 A | 12/1983 | Steer | |
| 4,425,130 A | 1/1984 | Desmarais | |
| 4,457,314 A | 7/1984 | Knowles | |
| 4,484,917 A | 11/1984 | Blackmon | |
| 4,496,355 A | 1/1985 | Hall | |
| 4,563,183 A | 1/1986 | Barrodale | |
| 4,568,339 A | 2/1986 | Steer | |
| 4,583,983 A | 4/1986 | Einhorn | |
| 4,615,692 A | 10/1986 | Giacalone | |
| 4,681,572 A | 7/1987 | Tokarz | |
| 4,747,166 A * | 5/1988 | Kuntz | A61F 5/455 |
| | | | 4/144.1 |
| 4,752,293 A | 6/1988 | Smith | |
| 4,759,753 A | 7/1988 | Schneider | |
| 4,795,449 A | 1/1989 | Schneider | |
| 4,813,943 A | 3/1989 | Smith | |
| 4,822,347 A | 4/1989 | Macdougall | |
| 4,846,819 A | 7/1989 | Welch | |
| 4,882,794 A | 11/1989 | Stewart, III | |
| 4,889,532 A | 12/1989 | Metz | |
| 4,889,533 A * | 12/1989 | Beecher | A61F 5/4407 |
| | | | 604/355 |
| 4,904,248 A | 2/1990 | Vaillancourt | |
| 4,936,838 A * | 6/1990 | Cross | A61F 5/455 |
| | | | 600/574 |
| 4,994,051 A | 2/1991 | Walsh | |
| 5,004,463 A | 4/1991 | Nigay | |
| 5,053,027 A | 10/1991 | Manfredi | |
| 5,091,998 A | 3/1992 | Witzke | |
| 5,263,947 A | 11/1993 | Kay | |
| 5,265,983 A | 11/1993 | Wennerstrom | |
| 5,267,988 A * | 12/1993 | Farkas | A61F 5/34 |
| | | | 4/144.3 |
| 5,674,212 A | 10/1997 | Osborn, III | |
| 5,678,564 A | 10/1997 | Lawrence | |
| 5,735,145 A | 4/1998 | Pernick | |
| 5,735,835 A | 4/1998 | Holland | |
| 5,833,678 A | 11/1998 | Ashton | |
| 5,911,222 A | 6/1999 | Lawrence | |
| 5,957,904 A | 9/1999 | Holland | |
| 5,966,748 A | 10/1999 | Young | |
| D418,918 S | 1/2000 | Cunningham | |
| 6,151,721 A | 11/2000 | Whitfield | |
| 6,183,454 B1 | 2/2001 | Levine | |
| 6,280,425 B1 | 8/2001 | Del Guercio | |
| 6,299,606 B1 * | 10/2001 | Young | A61B 10/007 |
| | | | 604/317 |
| 6,428,521 B1 | 8/2002 | Droll | |
| 6,461,340 B1 | 10/2002 | Lenker | |
| 6,537,262 B2 | 3/2003 | Thompson | |
| 6,569,133 B2 | 5/2003 | Cheng | |
| 6,592,560 B2 | 7/2003 | Snyder | |
| 6,702,763 B2 | 3/2004 | Murphy | |
| 6,716,181 B2 | 4/2004 | Spencer | |
| 7,018,366 B2 * | 3/2006 | Easter | A61F 5/451 |
| | | | 604/327 |
| 7,181,781 B1 | 2/2007 | Trabold | |
| 7,220,250 B2 | 5/2007 | Suzuki | |
| 7,358,282 B2 | 4/2008 | Krueger | |
| 7,361,803 B2 | 4/2008 | Miskie | |
| 7,445,615 B2 | 11/2008 | Mizutani | |
| 7,588,560 B1 | 9/2009 | Dunlop | |
| D627,878 S | 11/2010 | Bruns | |
| 8,262,632 B2 | 9/2012 | Faber | |
| 8,287,508 B1 | 10/2012 | Sanchez | |
| 8,303,554 B2 | 11/2012 | Tsai | |
| 8,388,588 B2 | 3/2013 | Wada | |
| 8,403,901 B2 | 3/2013 | Dunlop | |
| 8,454,570 B2 | 6/2013 | Carstens | |
| 9,028,460 B2 * | 5/2015 | Medeiros | A61F 5/451 |
| | | | 604/347 |
| 9,761,723 B2 | 9/2017 | Ching | |
| 10,226,376 B2 | 3/2019 | Sanchez | |
| 10,376,406 B2 | 8/2019 | Newton | |
| 10,376,407 B2 | 8/2019 | Newton | |
| 10,390,989 B2 | 8/2019 | Sanchez | |
| 2004/0068780 A1 * | 4/2004 | Scott | A47K 11/12 |
| | | | 4/144.1 |
| 2004/0236292 A1 * | 11/2004 | Tazoe | A61F 5/451 |
| | | | 604/317 |
| 2005/0033248 A1 * | 2/2005 | Machida | A61F 5/455 |
| | | | 604/327 |
| 2005/0137559 A1 | 6/2005 | Mizutani | |
| 2006/0015080 A1 * | 1/2006 | Mahnensmith | A61F 13/15 |
| | | | 604/327 |
| 2007/0214553 A1 * | 9/2007 | Carromba | A47K 11/12 |
| | | | 4/144.4 |
| 2008/0287894 A1 * | 11/2008 | Van Den Heuvel | A61F 5/455 |
| | | | 604/327 |
| 2009/0056003 A1 | 3/2009 | Ivie | |
| 2010/0198172 A1 | 8/2010 | Wada | |
| 2010/0234820 A1 * | 9/2010 | Tsai | A61F 5/4404 |
| | | | 604/385.03 |
| 2011/0054426 A1 | 3/2011 | Stewart | |
| 2011/0060299 A1 * | 3/2011 | Wada | A61F 5/455 |
| | | | 604/318 |
| 2011/0238023 A1 | 9/2011 | Slayton | |
| 2014/0276501 A1 | 9/2014 | Cisko | |
| 2014/0325746 A1 | 11/2014 | Block | |
| 2015/0359660 A1 | 12/2015 | Harvie | |
| 2016/0367226 A1 | 12/2016 | Newton | |
| 2016/0374848 A1 * | 12/2016 | Sanchez | A61F 5/453 |
| | | | 604/319 |
| 2017/0007438 A1 | 1/2017 | Harvie | |
| 2017/0143534 A1 | 5/2017 | Sanchez | |
| 2017/0202714 A1 | 7/2017 | Hurwitz | |
| 2017/0252014 A1 * | 9/2017 | Siller Gonzalez | A61B 10/007 |
| 2017/0252202 A9 | 9/2017 | Sanchez | |
| 2017/0266031 A1 | 9/2017 | Sanchez | |
| 2017/0281399 A1 | 10/2017 | Vanmiddendorp | |
| 2017/0348139 A1 | 12/2017 | Newton | |
| 2018/0015210 A1 * | 1/2018 | Rickman | A61F 13/4756 |
| 2018/0028348 A1 | 2/2018 | Newton | |
| 2018/0028349 A1 | 2/2018 | Newton | |
| 2018/0049910 A1 | 2/2018 | Newton | |
| 2018/0228642 A1 | 8/2018 | Davis | |
| 2019/0142624 A1 | 5/2019 | Sanchez | |
| 2019/0224036 A1 | 7/2019 | Sanchez | |
| 2019/0282391 A1 | 9/2019 | Johannes | |
| 2019/0307597 A1 | 10/2019 | Newton | |
| 2019/0307598 A1 | 10/2019 | Newton | |
| 2019/0314190 A1 | 10/2019 | Sanchez | |
| 2019/0365561 A1 | 12/2019 | Newton | |
| 2021/0236323 A1 | 8/2021 | Austermann | |
| 2021/0353450 A1 | 11/2021 | Sharma | |

FOREIGN PATENT DOCUMENTS

| | | |
|---|---|---|
| JP | 2001327527 | 11/2001 |
| JP | 4694149 | 6/2011 |
| WO | 2008063623 | 5/2008 |
| WO | 2016071894 | 5/2016 |
| WO | 2017209779 | 12/2017 |
| WO | 2018022414 | 2/2018 |

(56) References Cited

FOREIGN PATENT DOCUMENTS

| WO | 2018235065 | 12/2018 |
| WO | 2019212954 | 11/2019 |
| WO | 2020033699 | 2/2020 |

OTHER PUBLICATIONS

Communication Pursuant to Rule 164(1) EPC dated May 12, 2022 from corresponding European Patent Application No. 19848533.6; 14 pages.
FemMed Inc., GoGirl, http://go-girl.com/what-is-gogirl/, Feb. 23, 2018.
Rei, Sani-Fem Freshette Feminine Urinary Director, https://www.rei.com/product/407267/sani-fem-freshette-feminine-urinary-director, Feb. 26, 2018.
U.S. Appl. No. 14/947,759, dated Nov. 20, 2015, Raymond John Newton.
U.S. Appl. No. 62/084,078, dated Nov. 25, 2014, Robert A Sanchez.
Viscot Medical LLC, Patient Information & Instructions, The "Millie" Universal Urinal, 1990.
International Search Report and Written Opinion for International Application No. PCT/US2021/031494 dated Sep. 1, 2021.

* cited by examiner

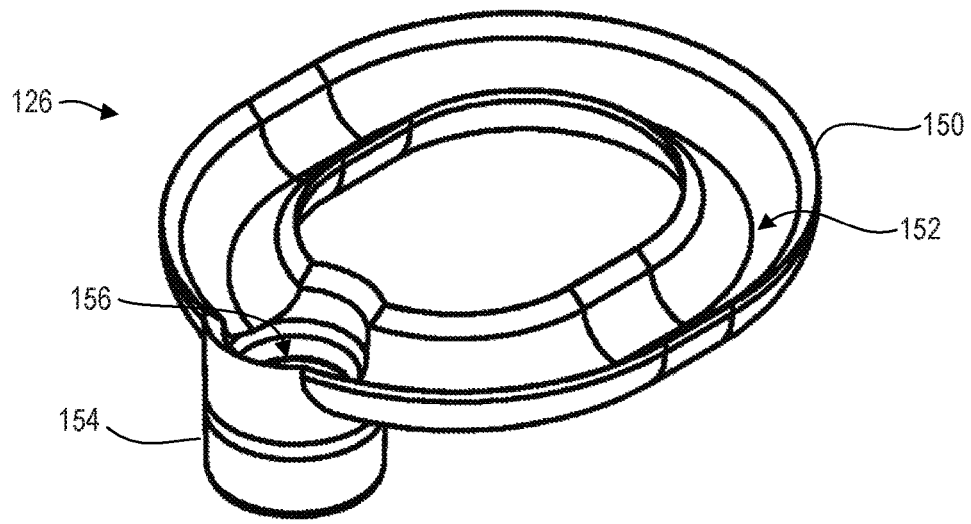
FIG. 38
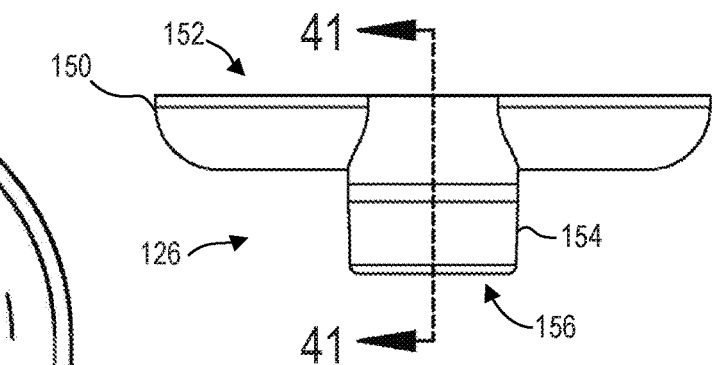
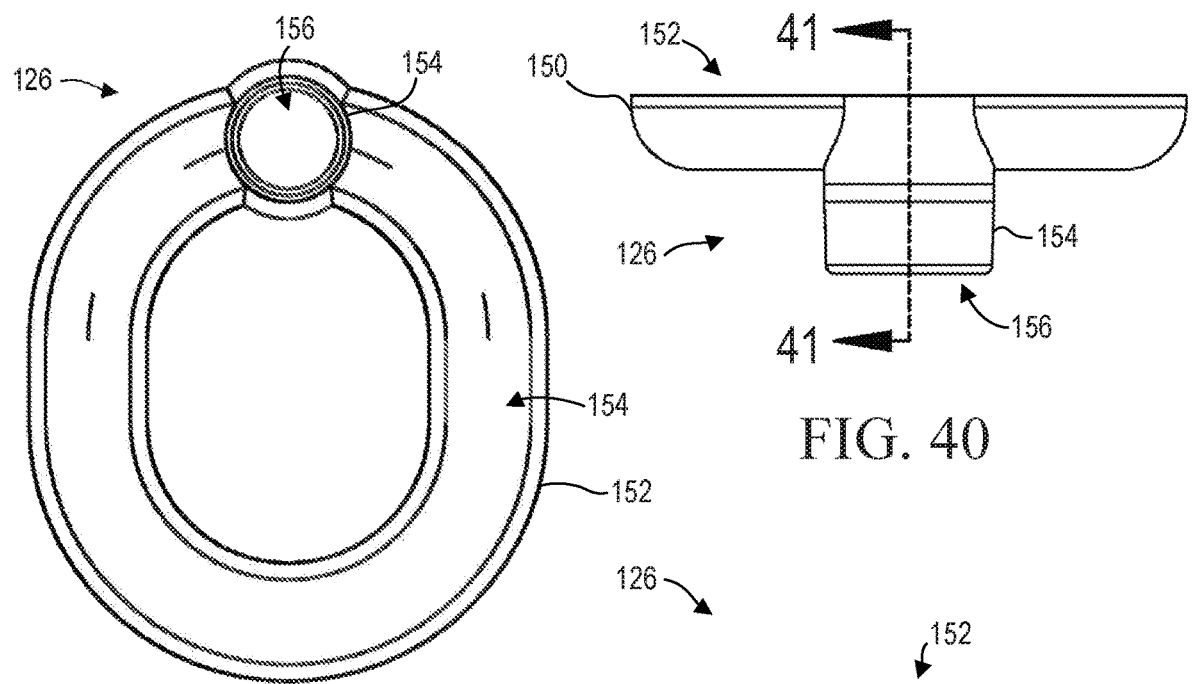
FIG. 39
FIG. 40
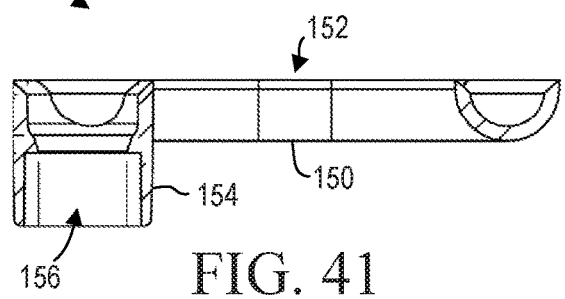
FIG. 41

FEMALE EXTERNAL URINARY DEVICE AND ASSEMBLY

CROSS-REFERENCE TO RELATED APPLICATIONS

This application claims the benefit of U.S. Provisional Application No. 62/716,543, filed Aug. 9, 2018, which is hereby incorporated by reference as if fully set forth herein.

TECHNICAL FIELD

The disclosure relates to the field of urine management, particularly in the health care and long-term care settings.

BACKGROUND

Urinary management is a critical need for both acute and long-term patient care. In the hospital setting, many patients, such as post-surgical patients, are unable to manage their urine flow during and immediately after surgery. A general solution to this issue is to catheterize the patient. Catheterization is advantageous when it is desired to monitor the urine output of a patient.

Catheterization is known to cause problems with nosocomial infections, and generally there are a high number of catheter-related urinary tract infections (CAUTI) annually. CAUTI is one of the most common nosocomial infections in hospitals and nursing homes, accounting for a major percentage of institutionally acquired infections. Catheterization also is an invasive procedure, albeit minimally. To address these issues, it is known to provide human urine aspiration systems that generally include an electric pump for applying suction to a urinal and for aspirating the urine to a storage canister. Generally, the patient is outfitted with a urinary collector that is secured at or near the patient. Upon activation of the pump, urine is caused to aspirate away from the patient and into the canister.

It is now desired to provide a female external urinary device and urine aspiration system, the urinary device being useful with known urine management aspiration systems. It has now been found that a urinary device, urinary device assembly, and system may be provided, along with a method for providing urinary management to a female. The urinary device generally comprises a core having a plurality of urine-receiving apertures and an interior suction channel that communicates with a suction aperture, preferably via a suction tube. The urinary device further includes an absorbent layer and fabric cover, and desirably includes other features as described in more detail hereinbelow.

BRIEF DESCRIPTION OF THE DRAWINGS

FIG. 38 is a perspective view of a collector of the core of the third alternative embodiment of a urinary device.

FIG. 39 is a top plan view of the collector of the core of the third alternative embodiment of a urinary device.

FIG. 40 is a front elevation view of the collector of the core of the third alternative embodiment of a urinary device.

FIG. 41 is a cross-sectional view of the collector of the core of the third alternative embodiment of a urinary device taken along the line 41-41 of FIG. 40.

DETAILED DESCRIPTION

Described herein in one aspect is a female external urinary device that includes a core, an absorbent layer disposed externally with respect to the core, and a fabric cover that at least partially covers the core and the absorbent layer. The core includes a non-absorbent material having a plurality of urine-receiving apertures. The core further includes a suction channel communicating with a suction aperture and including a reservoir fluidically communicating with the suction channel.

Also described herein, in another aspect, is a method that includes providing the previously-described urinary device assembly and securing the urinary device assembly to a female patient by positioning the urinary device assembly in a urine-retaining region and positioning the pelvic belt proximal a pelvic area of the patient. The method further includes aspirating urine away from the urinary device using suction.

Also described herein, in another aspect, is a urinary device assembly for securing to a patient. The urinary device assembly includes a pelvic belt and a urinary device releasable securable to the pelvic belt. The urinary device includes a core, an absorbent layer disposed externally with respect to said core; and a fabric cover that at least partially covering said core and said absorbent layer. The core includes a non-absorbent material having a plurality of urine-receiving apertures. The core further includes a suction channel communicating with a suction aperture and includes a reservoir fluidically communicating with said suction channel.

Also described herein, in another aspect, is a urinary device assembly including a core. The core includes an upper core layer having a guide that at least partially extends about at least one aperture disposed through the upper core layer. The core further includes a lower core layer disposed in at least partial engagement with the upper core layer. The core further includes a collector disposed between the upper core layer and the lower core layer in at least partial alignment with the at least one aperture. The urinary device assembly further includes a tube secured to the collector to direct fluid away from the collector.

Figure 1:
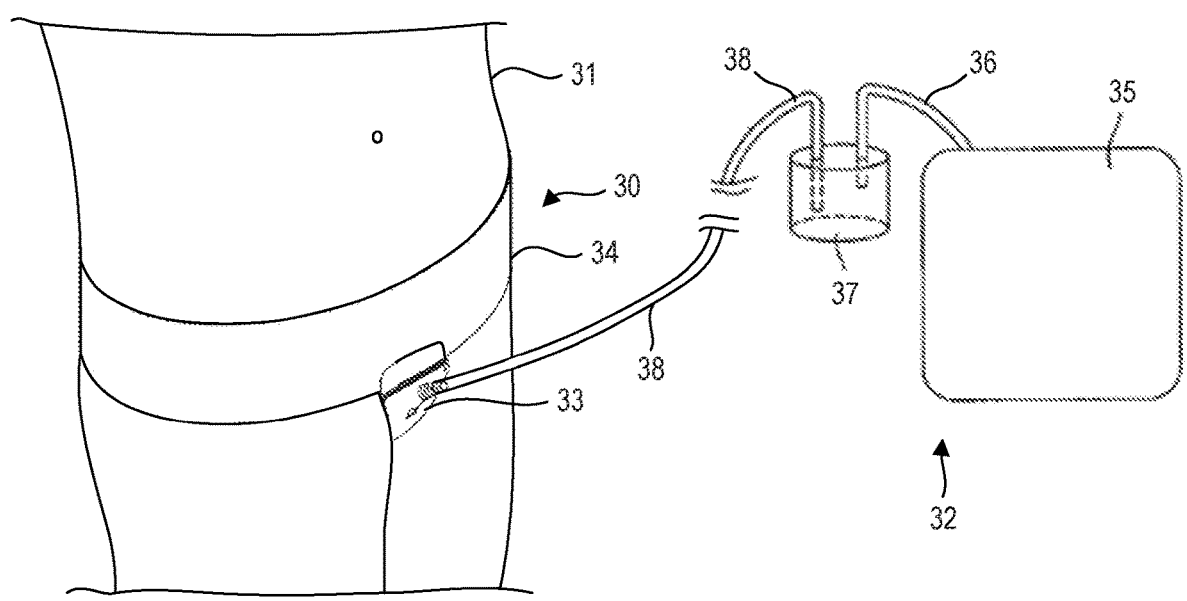
FIG. 1 is a perspective view illustrating the urinary device assembly of one embodiment secured to a female patient and illustrating schematically other components of a urine aspiration system.

With reference now to FIG. 1, a urinary device assembly 30 is secured to a patient 31 (e.g., a female patient) and forms part of overall urine aspiration system 32. The urinary device assembly 30 includes urinary device 33 and pelvic belt 34 positioned for securement to the patient 31. Other components of the urine aspiration system 32 include a pump 35, which provides a source of suction via pump suction tube 36, a urine reservoir, which takes the form of a canister 37, and a canister suction tube 38 that fluidically communicates with the urinary device 33, as described in more detail hereinbelow. In operation, a caregiver secures the pelvic belt 34 to the patient 31 proximal to the patient's pelvic area, and positions the urinary device 33 in a urine-receiving position generally between the legs of the patient, as illustrated in FIG. 1. For non-ambulatory patients, it is generally desired to employ the complete system, and therefore to secure the canister suction tube 38 to the urinary device and to operate the pump 35 such that urine admitted from the patient 31 will be drawn through the canister suction tube 38 and into the canister 37. The pump 35 may be a separate pump as part of a standalone system, or may be a component of house vacuum in a hospital setting. As described in more detail below, the urinary device 33 may be employed for ambulatory patients, in which case the remaining components of the assembly generally are not employed.

Figure 2:
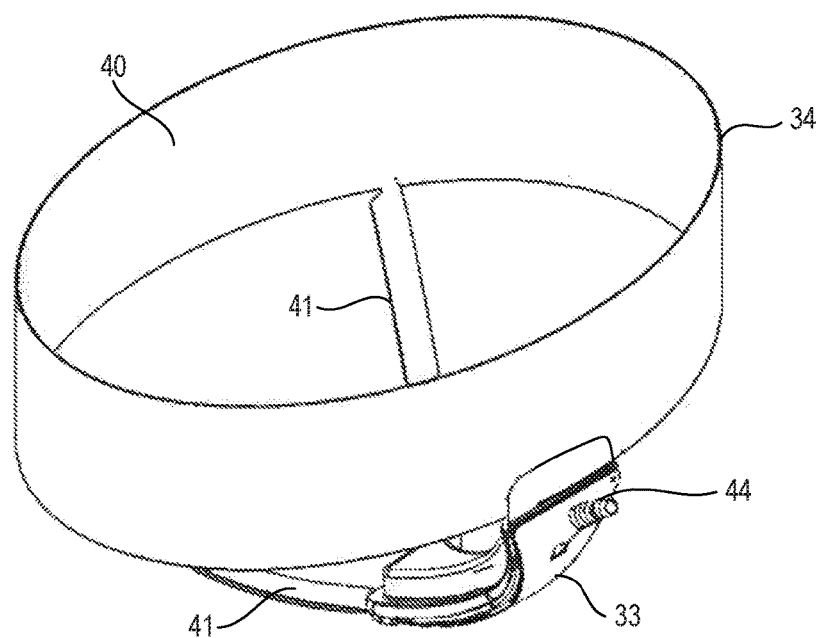
FIGS. 2 and 3 are perspective views of the urinary device assembly illustrated in FIG. 1
Figure 3:
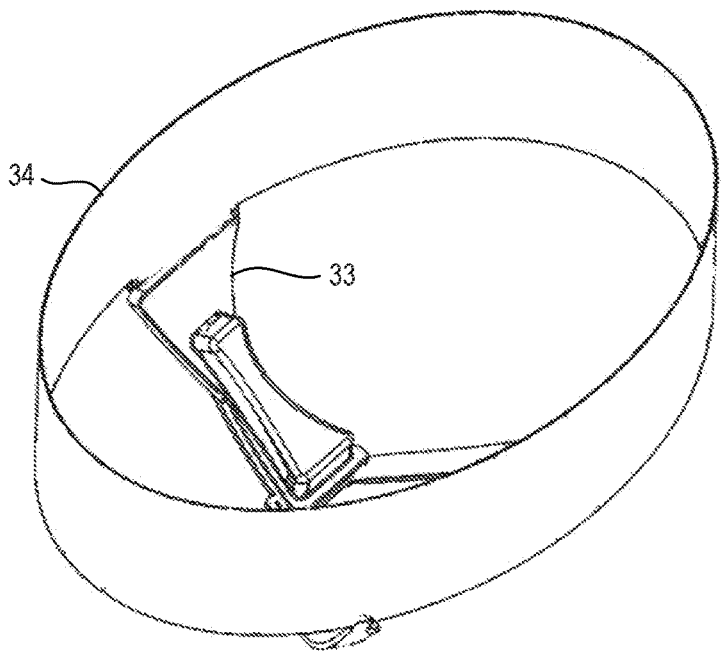
Figure 4:
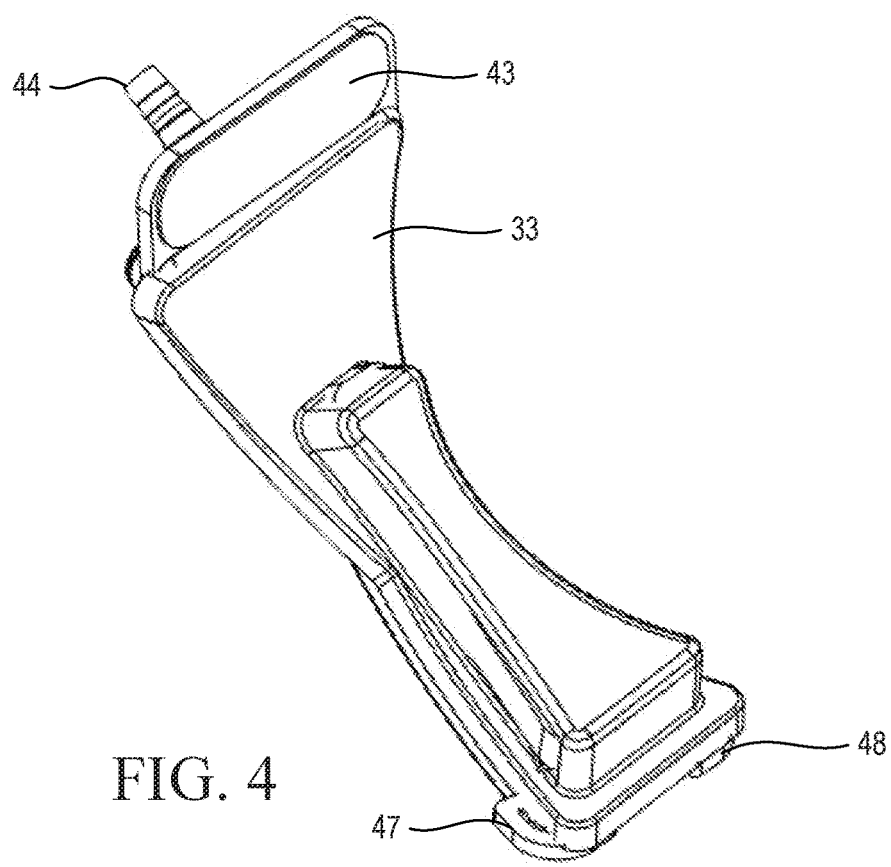
FIG. 4 is a perspective view of the external urinary device of the urinary device assembly illustrated in FIG. 1.
Figure 5:
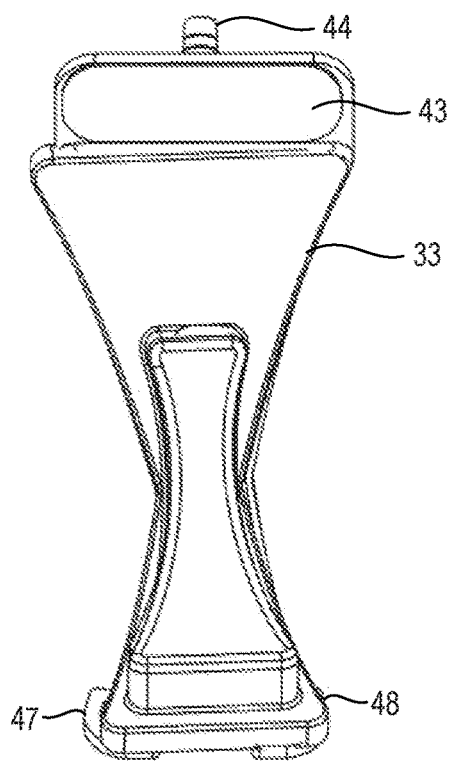
FIG. 5 is a front elevation of the urinary device illustrated in FIG. 4.
Figure 6:
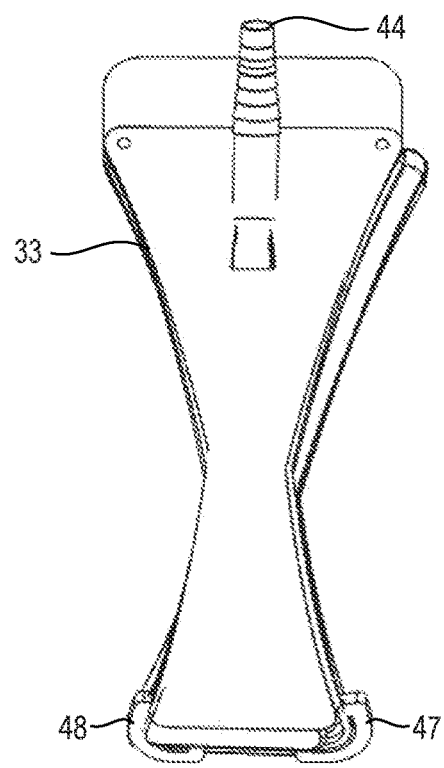
FIG. 6 is a rear elevation of the urinary device illustrated in FIG. 4.
Figure 7:
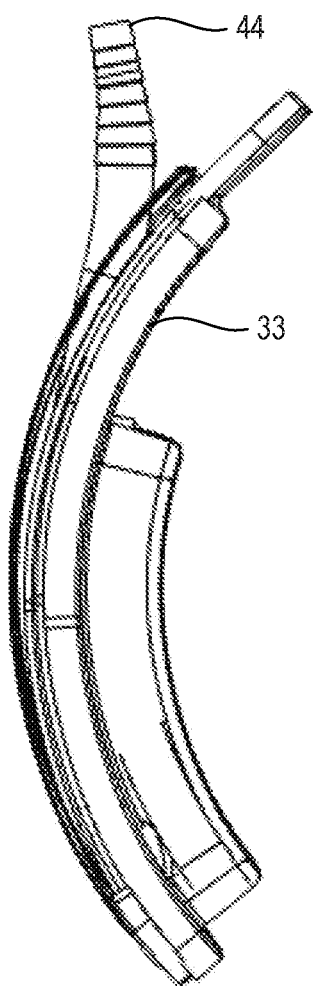
FIG. 7 is a first side elevation.
Figure 8:
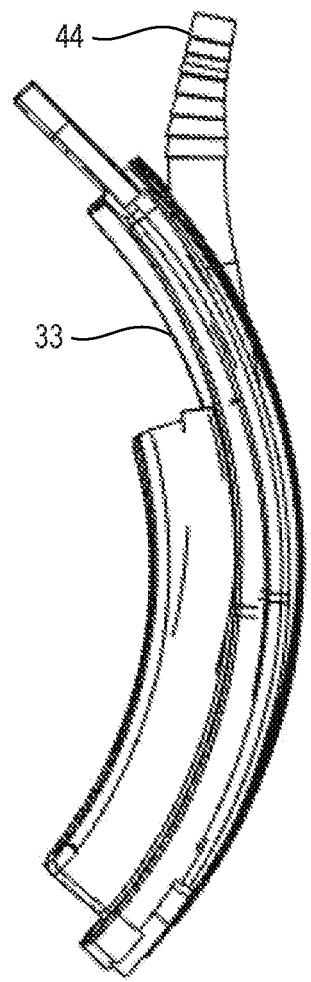
FIG. 8 is a second side elevation, of the urinary device illustrated in FIG. 4.
Figure 9:
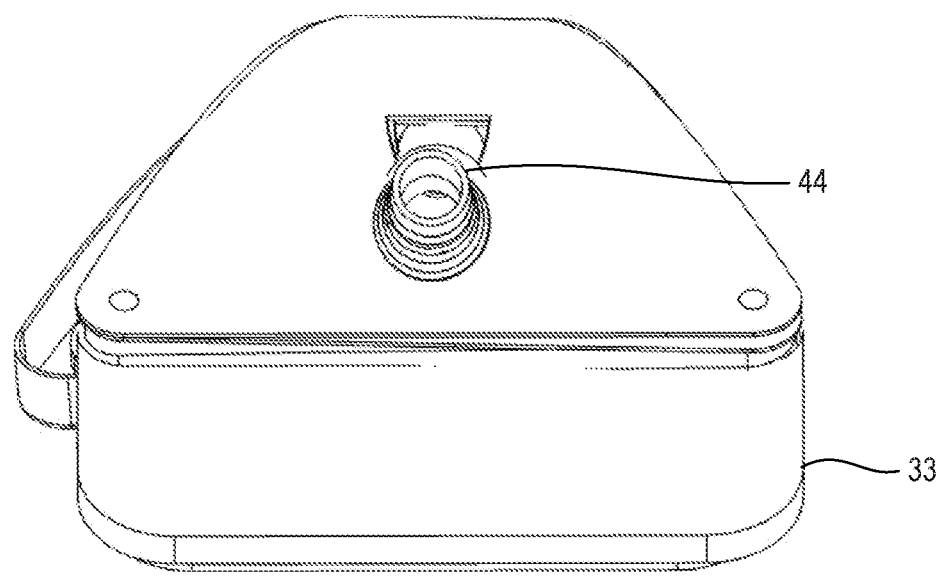
FIG. 9 is a top plan view.
Figure 10:
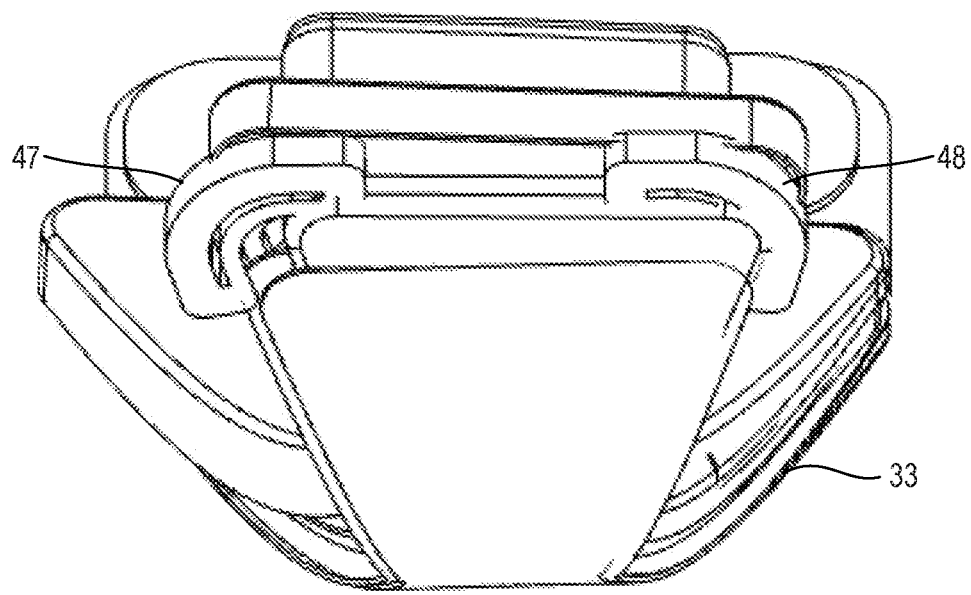
FIG. 10 is a bottom plan view, of the urinary device illustrated in FIG. 4.

The pelvic belt 34 is further illustrated in FIGS. 2 and 3. As seen, the pelvic belt 34 includes a main belt portion 40, which circumnavigates the patient, and one or more strap portions 41, which are secured to the urinary device 33. With further reference to FIGS. 4-10, the urinary device 33 includes an area of hook or loop material 43 (FIGS. 4 and 5) that is secured to mating loop or hook material (not separately shown) on the pelvic belt 34, the connection forming a hook-and-loop connection. The pelvic belt 34 may be designed such that the urinary device 33 may be secured to an exterior or to an interior surface of the pelvic belt 34; as illustrated, the urinary device 33 is secured to the interior surface. FIGS. 2 and 4-9 illustrate a suction spout 44 that communicates with the interior of the urinary device 33. The suction spout 44 is further illustrated in FIGS. 4-9, which further illustrate the area of hook or loop material 43 (FIG. 5 only). As seen in FIGS. 4-6, the urinary device 33 includes at least one strap retainer 47. In the illustrated embodiment, the urinary device 33 includes a pair of strap retainers 47, 48 which take the form of loops through which the strap portions 41 of the pelvic belt 34 may be passed.

Figure 11:
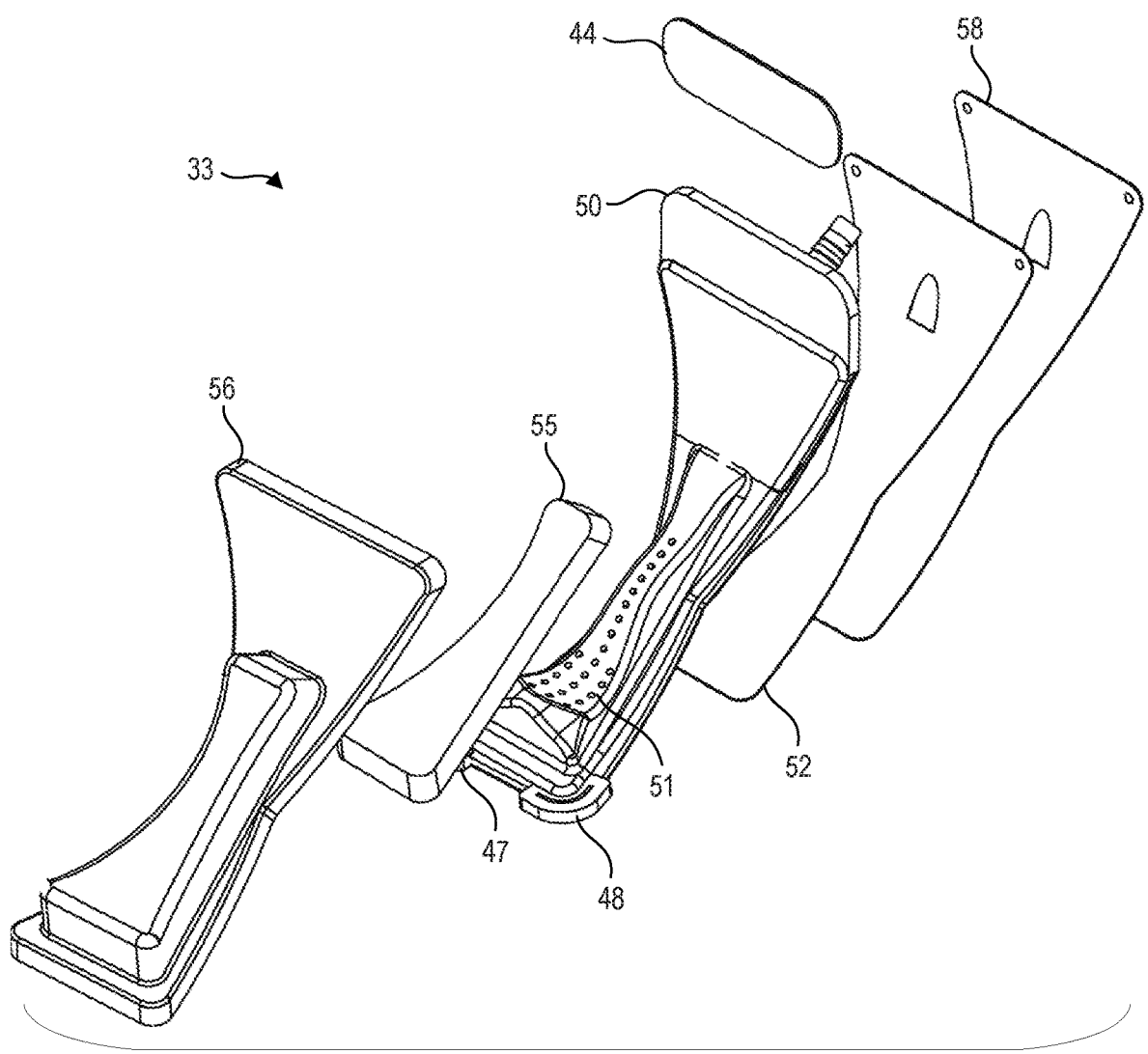
FIG. 11 is an exploded view of the urinary device illustrated in FIG. 4.

The construction of the urinary device 33 is further seen with reference to FIG. 11. As shown, the urinary device 33 includes a core 50 that comprises a non-absorbent material and a plurality of urine-receiving apertures 51. As illustrated, the uppermost apertures are less numerous across the width of the device than the lowermost apertures. Disposed externally with respect to the core 50 is an absorbent layer 52, which may be any absorbent material, such as that used in the ULTRASORB or CAPRI PLUS products sold by Medline Industries, Inc. of Northfield, Illinois. These products include superabsorbent materials that retain liquids. Superabsorbent polymers are materials that imbibe or absorb at least ten times their own weight in aqueous fluid and that retain the imbibed or absorbed aqueous fluid under moderate pressure. Many superabsorbent materials are known in the art, and thus, for example, starch-nitrile materials may be employed in the absorbent layer 52.

Disposed inwardly with respect to the core is a soaker layer 55. The soaker layer 55 is a moderately absorbent layer that is intended to provide a moderate amount of absorbency to assist in distributing fluid across the length and width of the core 50, and also to absorb small amounts of urine for ambulatory patients, for which suction typically will not be applied during ambulation. The soaker layer 55 preferably is composed of a non-absorbent fiber, such as polyester, and an absorbent fiber, such as rayon. For instance, the soaker layer may be composed of polyester and rayon fibers in a ratio ranging from 70:30 to 98:2, preferably to 95:5, expressed as a ratio of polyester:rayon. The soaker layer 55, core 50, and absorbent layer 52 are at least partially covered by a fabric cover, the fabric cover in this embodiment comprising an inner cover layer 56 and an outer cover layer 58 that are secured together such as by stitching, welding, or gluing to thereby contain the other components of the urinary device. As seen in FIG. 11 and with returning reference to FIG. 5, portions of the core 50 extend outside the fabric cover and include the strap retainers 47, 48 and the area of hook or loop material 43. The soaker layer 55 covers at least a majority of the urine-receiving apertures 51, and preferably all of the urine-receiving apertures 51, in the core 50.

With reference now to FIGS. 12-16, the core 50 includes a urine-receiving portion 60, a pelvic portion 61, and a superseding portion 62 upon which is placed the hook or loop material (not shown in FIGS. 12-16). The core 50 includes the plurality of urine-receiving apertures 51 that, in the illustrated embodiment, are disposed in two sections, a narrower upper section comprising a single row of apertures and a wider bottom section that includes in this embodiment five rows of three apertures. Integrally molded with the core are the strap retainers 47, 48 that are intended to receive the strap portion 41 of the pelvic belt 34.

Figure 13:
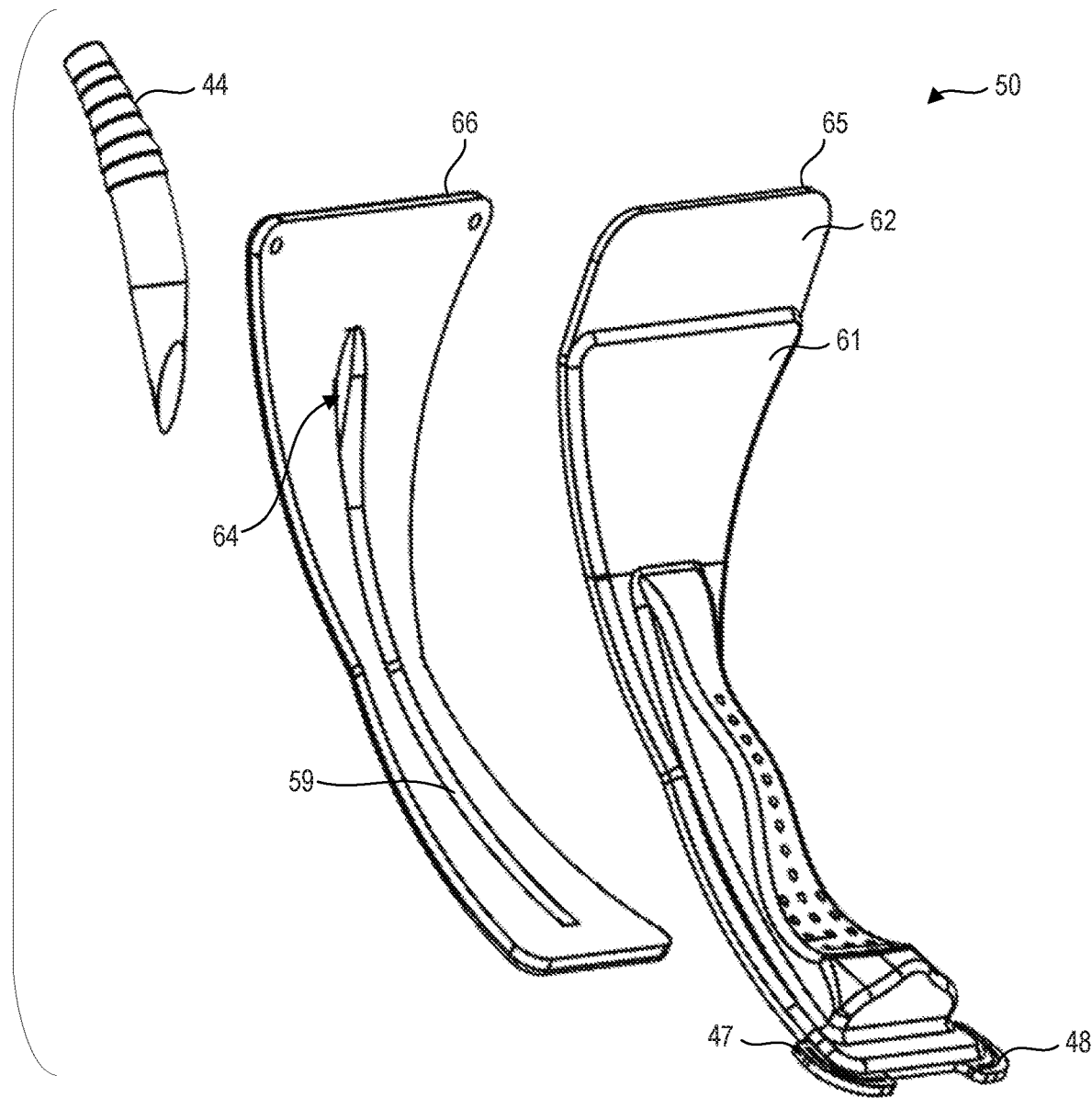
FIG. 13 is a first exploded view of the core illustrated in FIG. 12.
Figure 14:
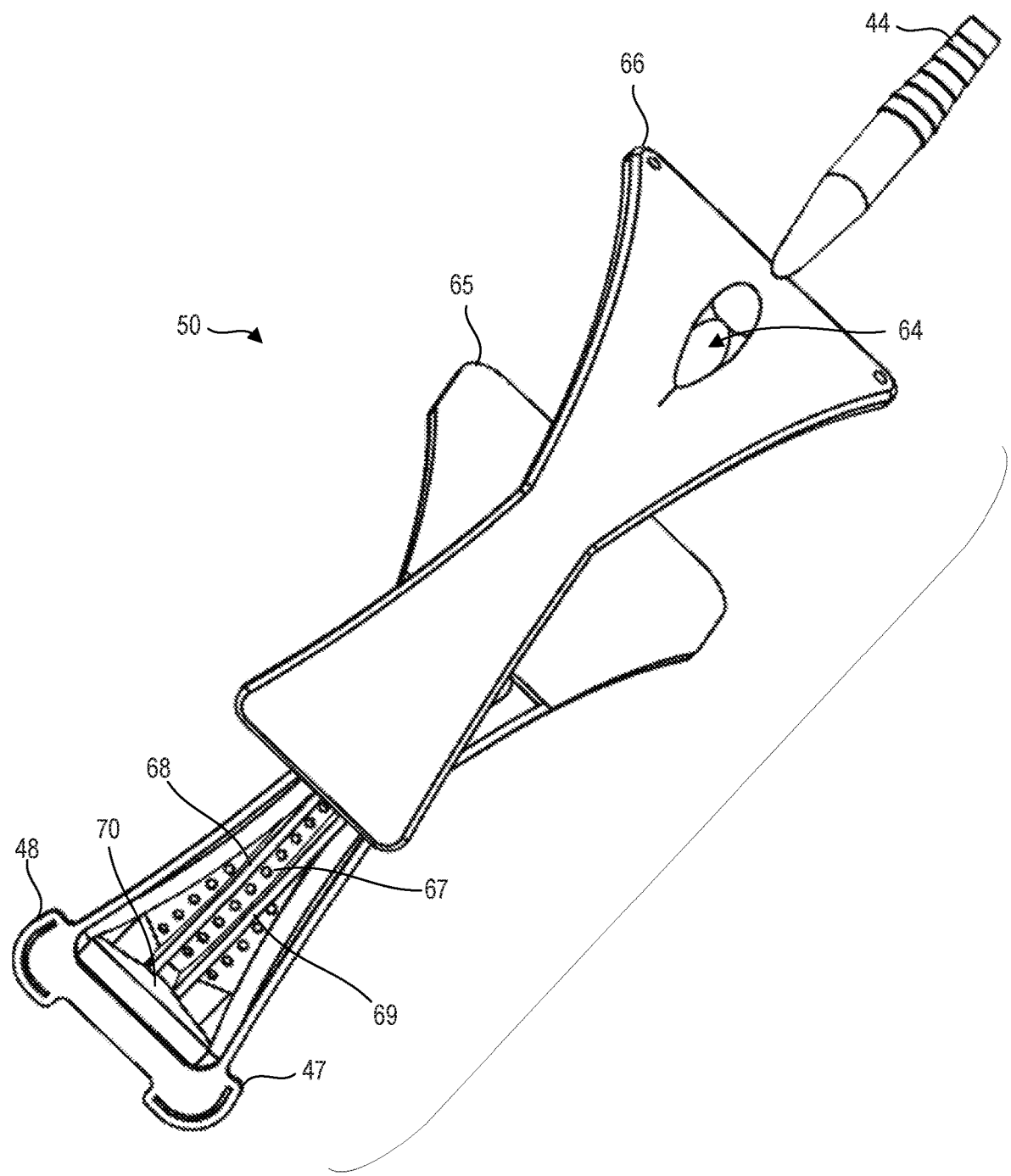
FIG. 14 is a second exploded view of the core illustrated in FIG. 12.
Figure 15:
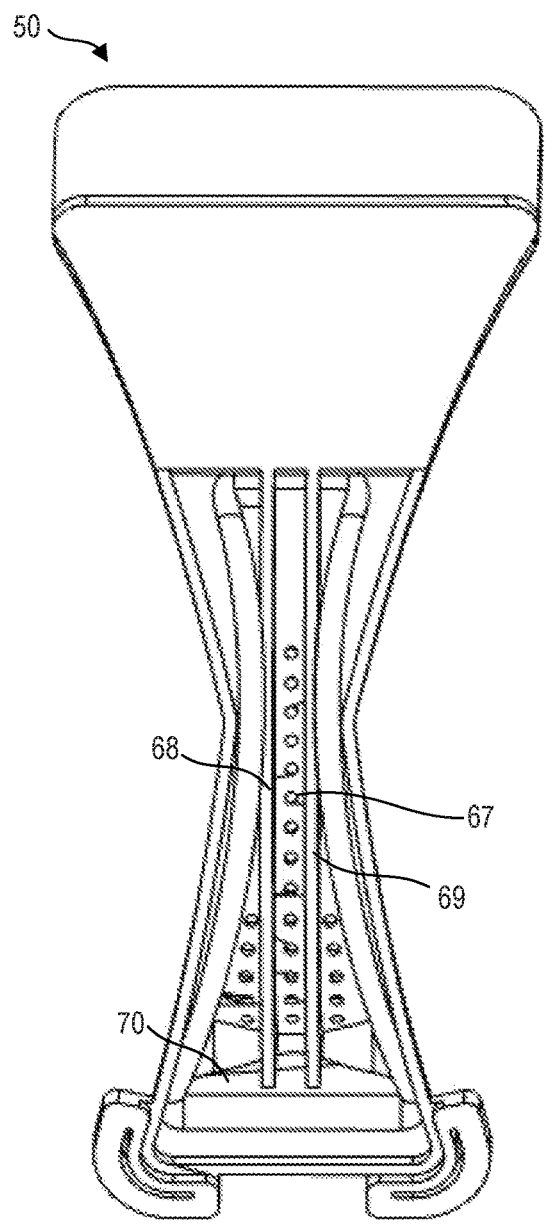
FIG. 15 is a rear elevation of the core illustrated in FIG. 12 with the cover of the core removed.
Figure 16:
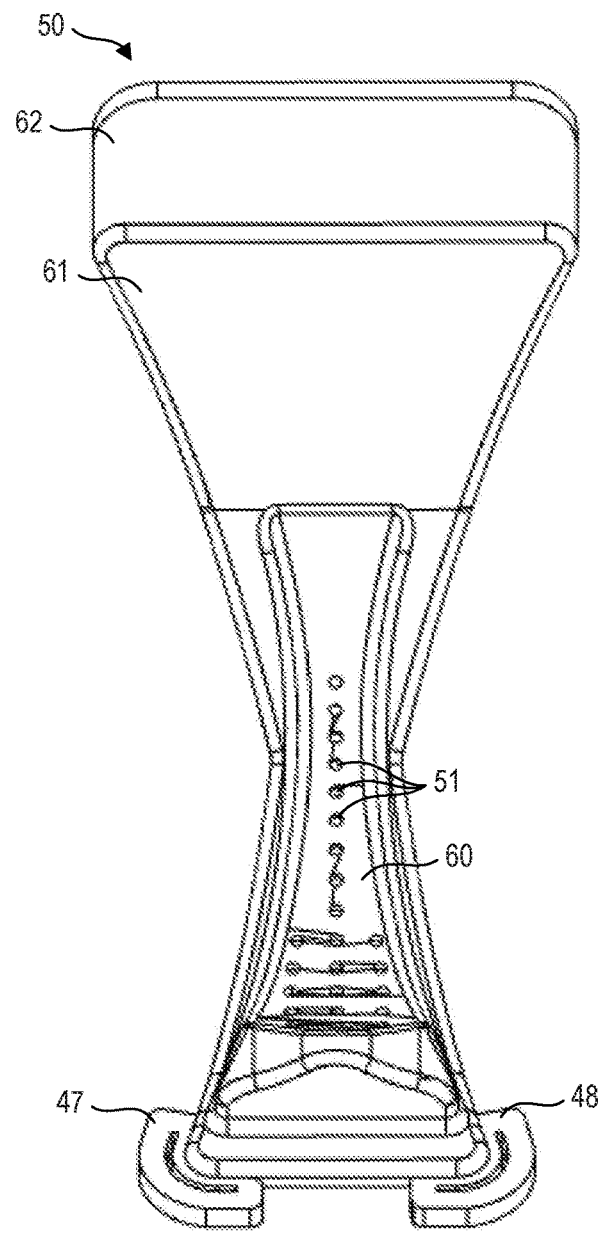
FIG. 16 is a front elevation of the core illustrated in FIG. 12.
Figure 17:
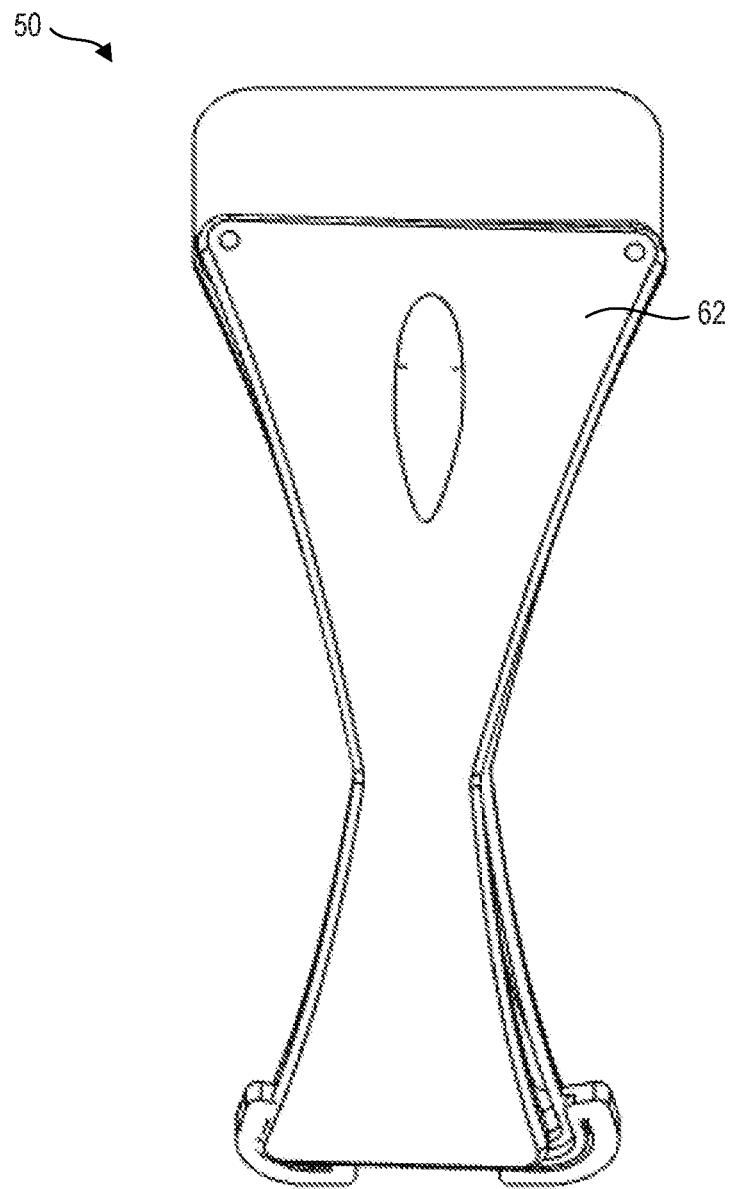
FIG. 17 is a rear elevation of the core illustrated in FIG. 12.
Figures 18, 19:
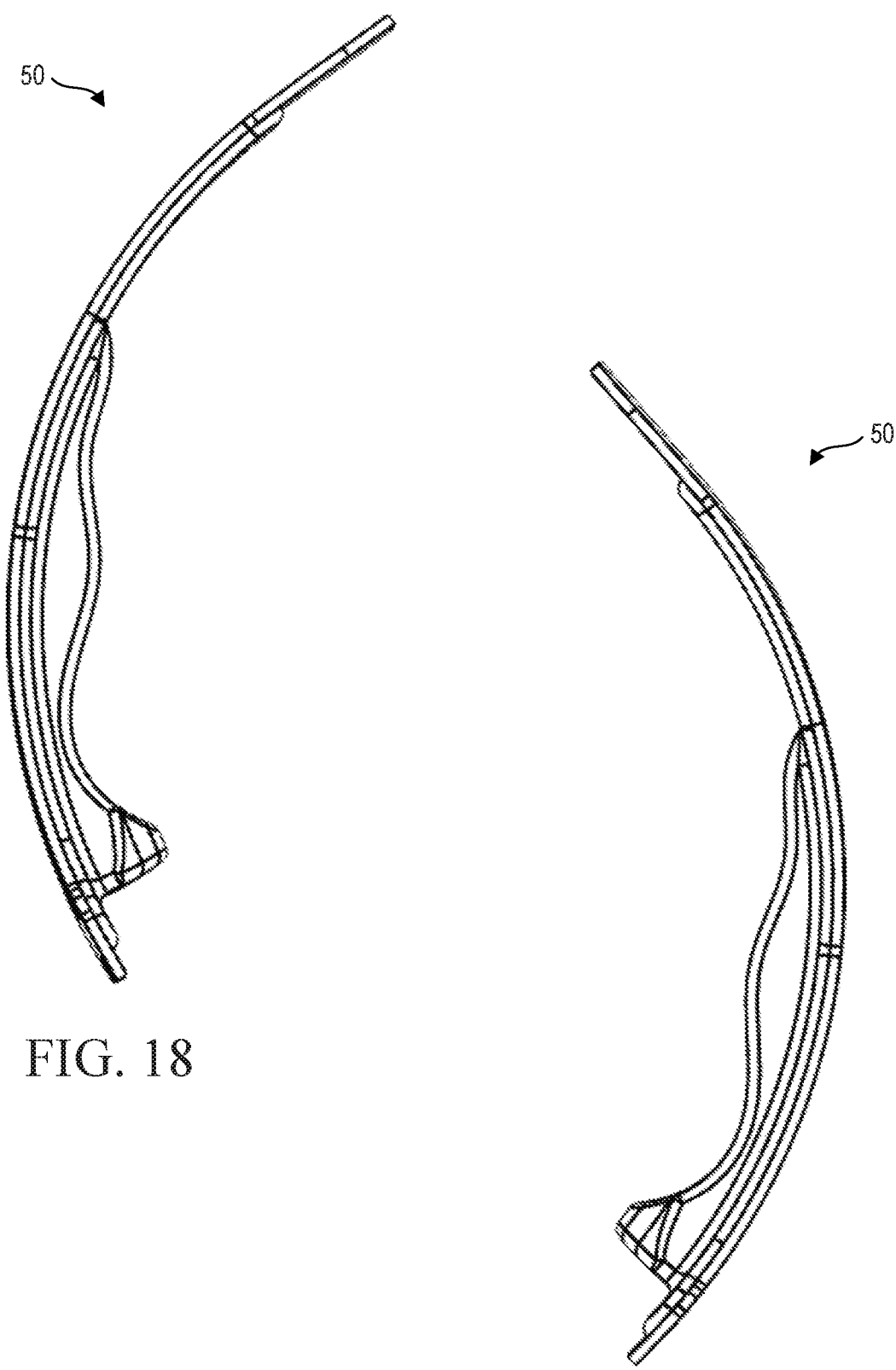
FIG. 18 is a first side elevation.
FIG. 19 is a second side elevation, of the core illustrated in FIG. 12.
Figure 20:
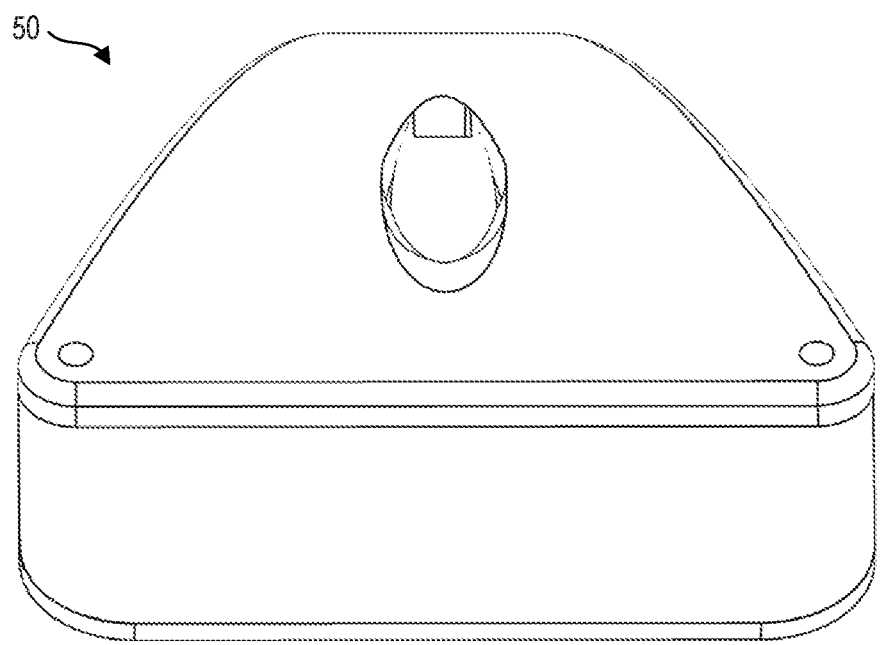
FIG. 20 is a top plan view.
Figure 21:
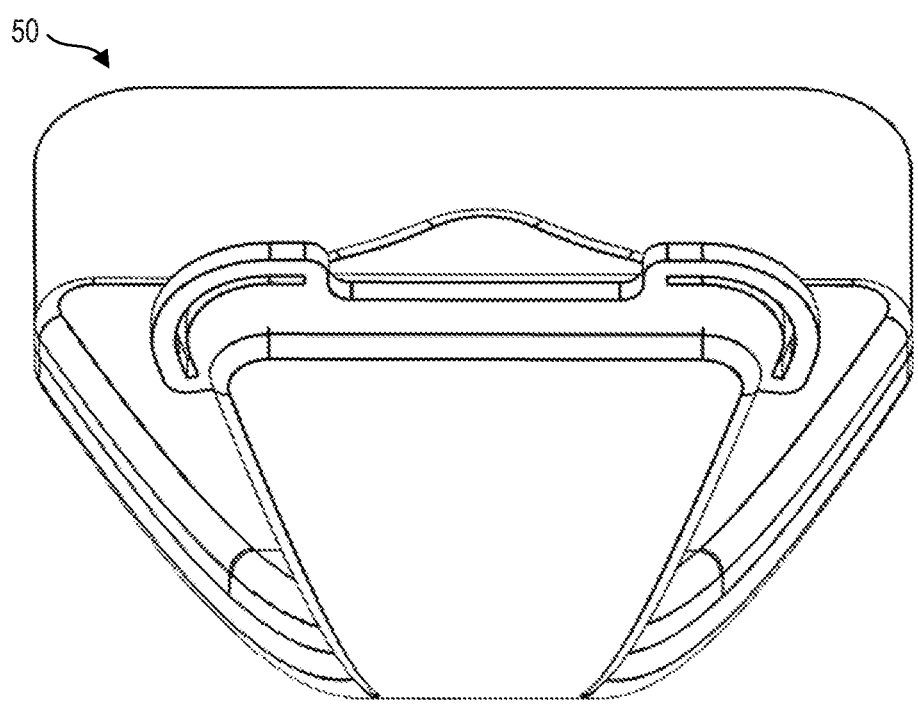
FIG. 21 is a bottom plan view, of the core device illustrated in FIG. 12.
Figure 22:
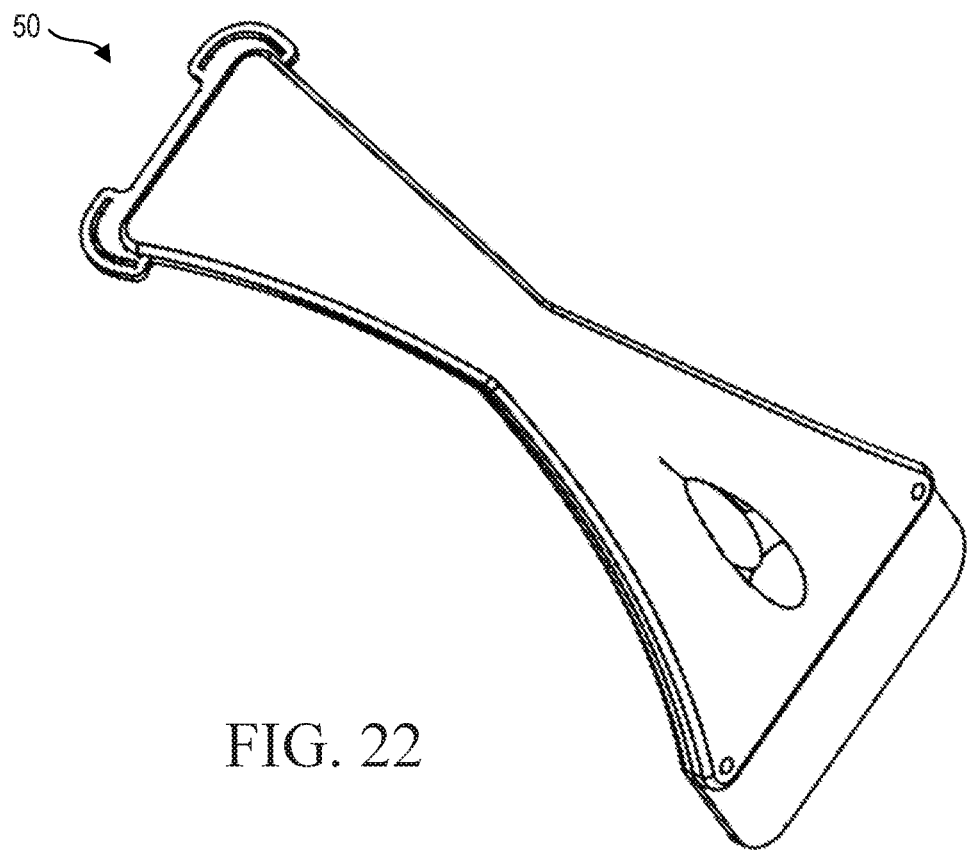
FIGS. 22 and 23 are additional perspective views of the core illustrated in FIG. 12.
Figure 23:
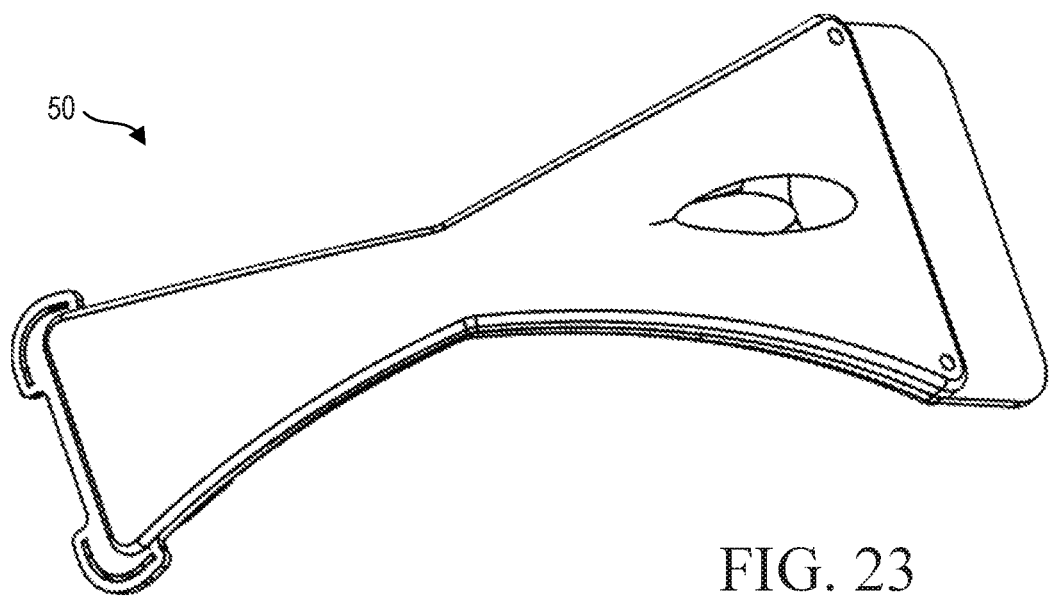

With particular reference to FIGS. 13-15, the core 50 comprises an inner core section 65 and an outer core section 66, the outer core section 66 having an aperture 64 for receiving the spout 44. The outer core section 66 includes an outer core section channel portion 59 (shown in FIG. 13) that corresponds to an inner core section channel portion 67 (shown in FIGS. 14 and 15) to thereby define a suction channel. The inner core section channel portion 67 is partially defined by ribs 68, 69 which terminate at a reservoir area 70. Via this arrangement, when suction is applied to the spout 44, urine is aspirated out of the reservoir area 70 and through the suction channel that is formed when the inner core section 65 and outer core section 66 meet. Any urine in the reservoir area 70 is aspirated into the suction channel and away from the patient through the spout 44. The suction channel is believed to provide more effective aspiration than would be attained absent the suction channel under the typical suction pressures seen in hospital settings. Notably, the reservoir area 70 will store a small amount of urine in the absence of suction, such as in the case of an ambulatory patient. Spillage or overage of urine is addressed by the absorbent layer 52 that is provided to absorb urine that is not tracked by the reservoir area 70 and that escapes from the core 50. It is contemplated that the urinary device 33 will permit the patient a moderate amount of ambulation before the reservoir area 70 absorbent layer 52 become full.

Figure 12:
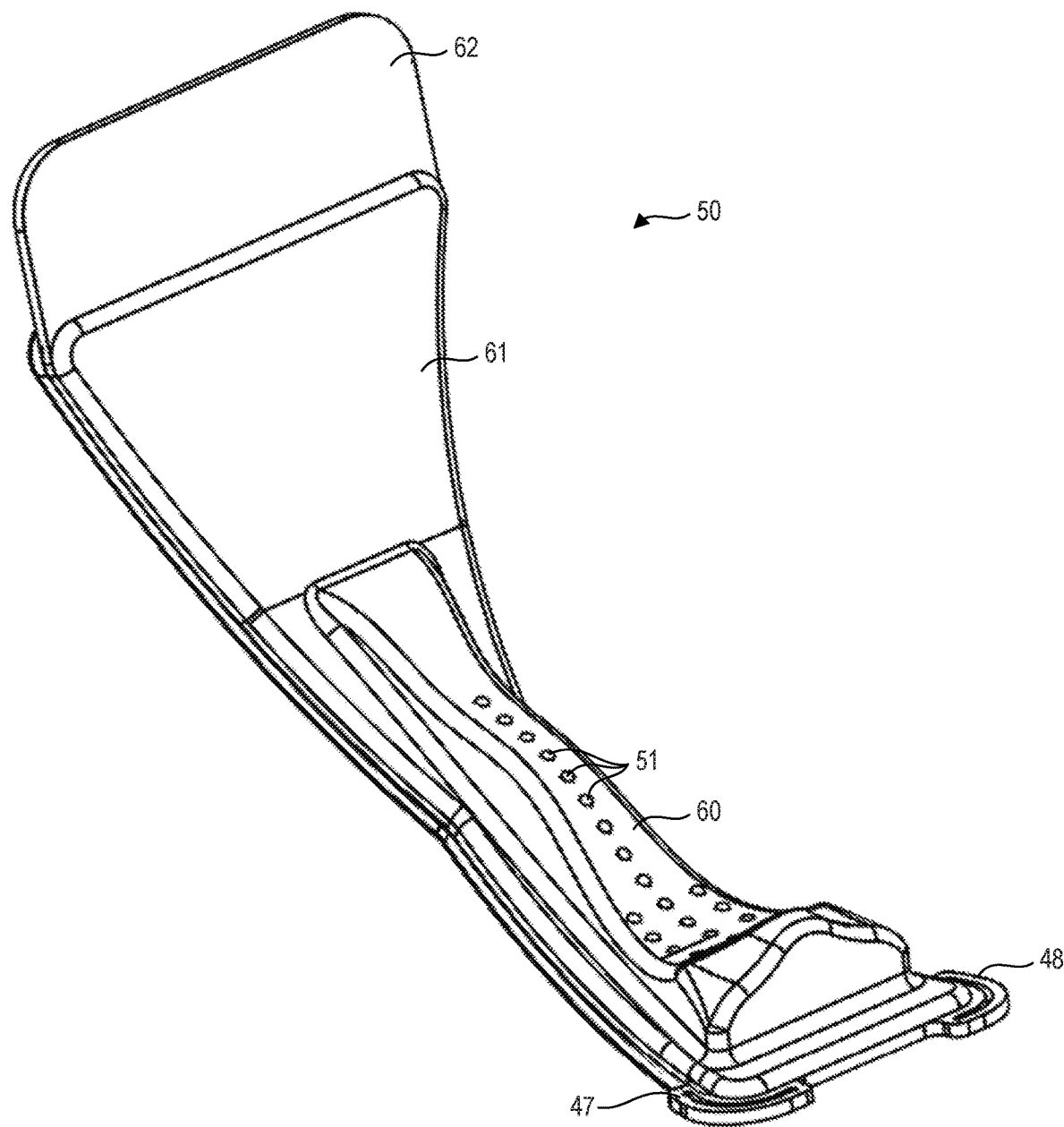
FIG. 12 is a perspective view of the core of the urinary device illustrated in FIG. 4.
Figure 24:
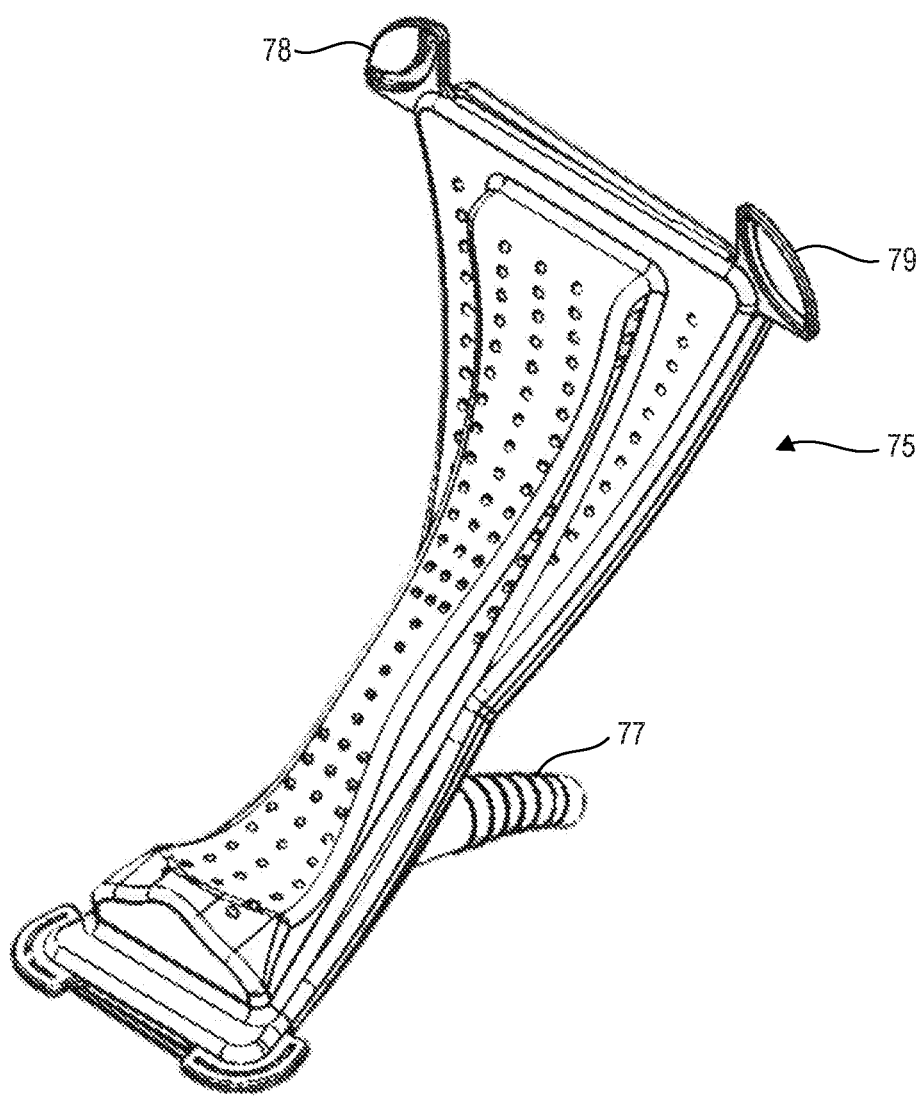
FIG. 24 is a perspective view of the core of a first alternative embodiment of the urinary device.
Figure 25:
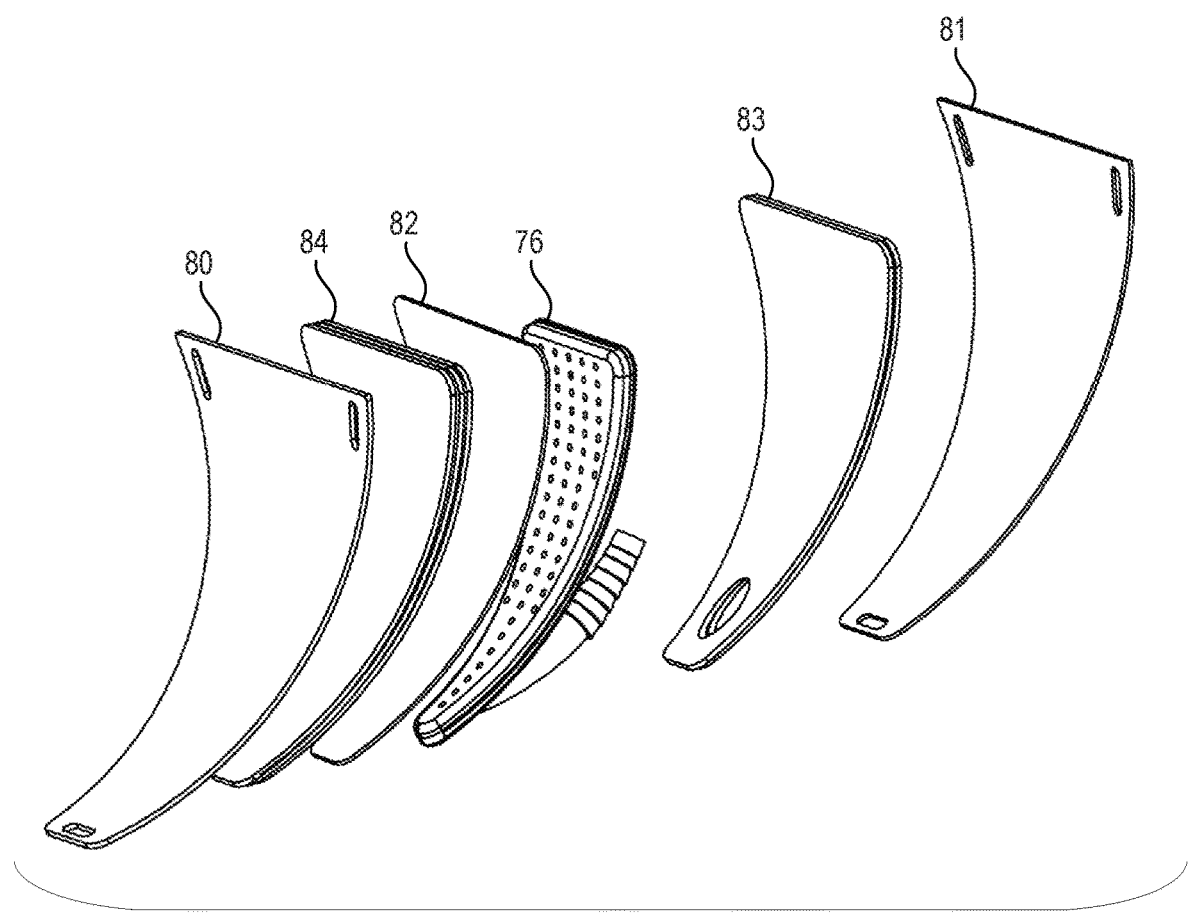
FIG. 25 is an exploded view of a second alternative embodiment of a urinary device.

The core 50 may be shaped otherwise than as shown in FIG. 12. For example, as shown in FIGS. 24 and 25, alternative cores 75, 76 may be employed. As seen in FIG. 24, for instance, the vertical position of the spout 77 is not critical and indeed the spout may be placed at various positions along the height of the core. The core 75 illustrated in FIG. 24 includes a number of additional urine-receiving apertures and includes flat portions 78, 79 on which may be provided hook or loop material for mating with corresponding loop or hook material on a pelvic belt (not illustrated). As seen in FIG. 25, the apertures on the core 76 may be positioned in an array such that the lowermost apertures are less numerous across the width of the device than the uppermost apertures, in contrast to the core 50 illustrated in FIG. 12. The urinary device shown in FIG. 25 includes the core 76, inner and outer fabric layers 80, 81, soaker layer 82, absorbent layer 83, and an optional additional absorbent layer 84 disposed inwardly of the core 76 and the soaker layer 82.

The cores described herein may be made of any suitable non-absorbent material, such as polyethylene. Any suitable fabric cover may be employed, such as a woven cotton cloth material. The pelvic belt may be made of any suitable material, preferably an elastic medical-grade material, and the pump, urine canister, and tubing may be conventional. It is therefore seen that the female external urinary device provided hereinabove is versatile and compatible with many existing urine management systems.

Figure 26:
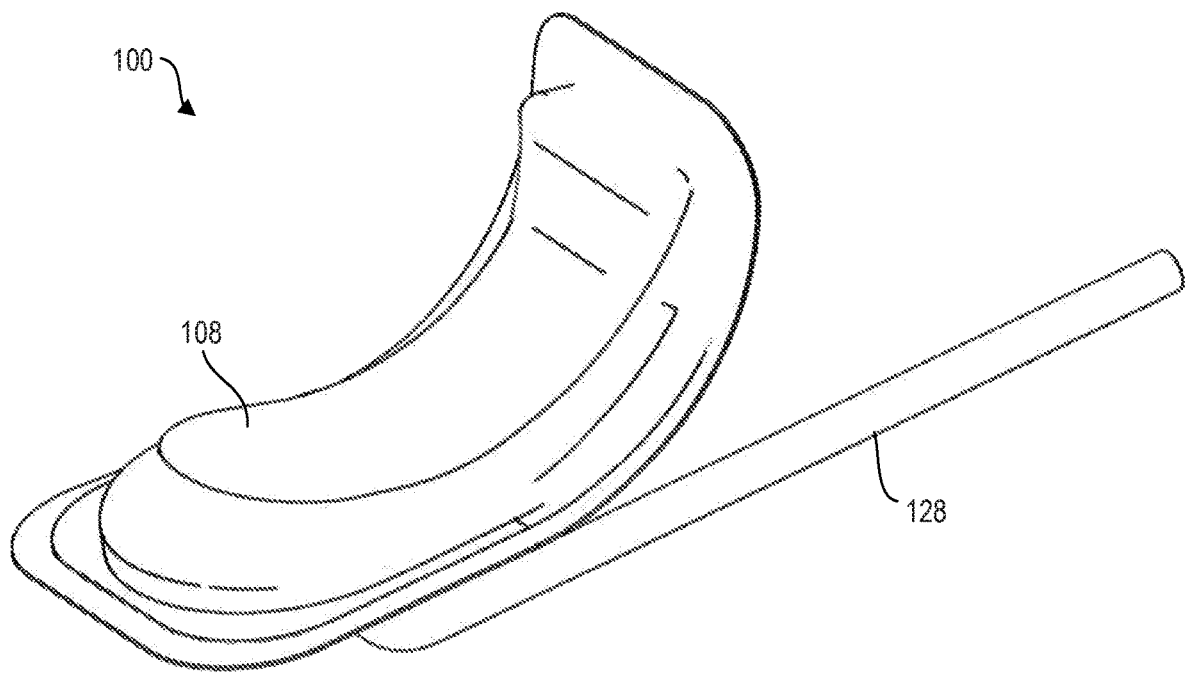
FIG. 26 is an upper perspective view of a third alternative embodiment of a urinary device.
Figure 27:
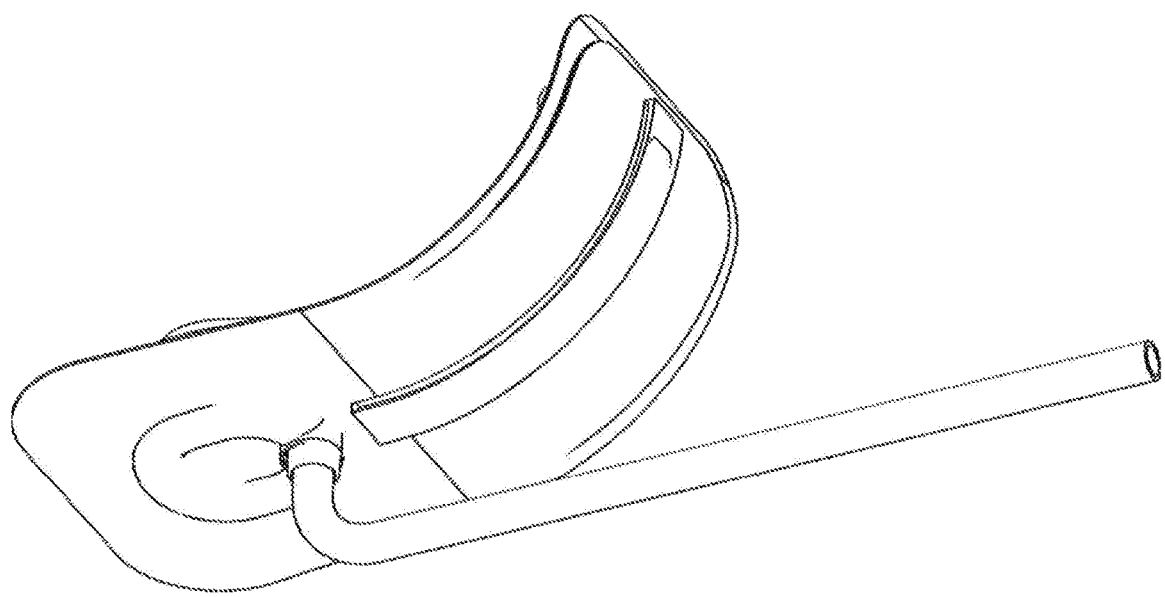
FIG. 27 is a lower perspective view of a third alternative embodiment of a urinary device.

With reference now to FIGS. 26 and 27, another urinary device 100 is shown. The urinary device 100 may be used in place of urinary device 33 in the urinary device assembly 30 of the urine aspiration system 32 discussed with respect with FIGS. 1-25.

The urinary device 100 may be an assembly that includes a lower cover, referred to herein as bottom cover 102, a core 104, a liquid transfer layer 106, and an upper cover, referred to herein as top cover 108.

Figure 28:
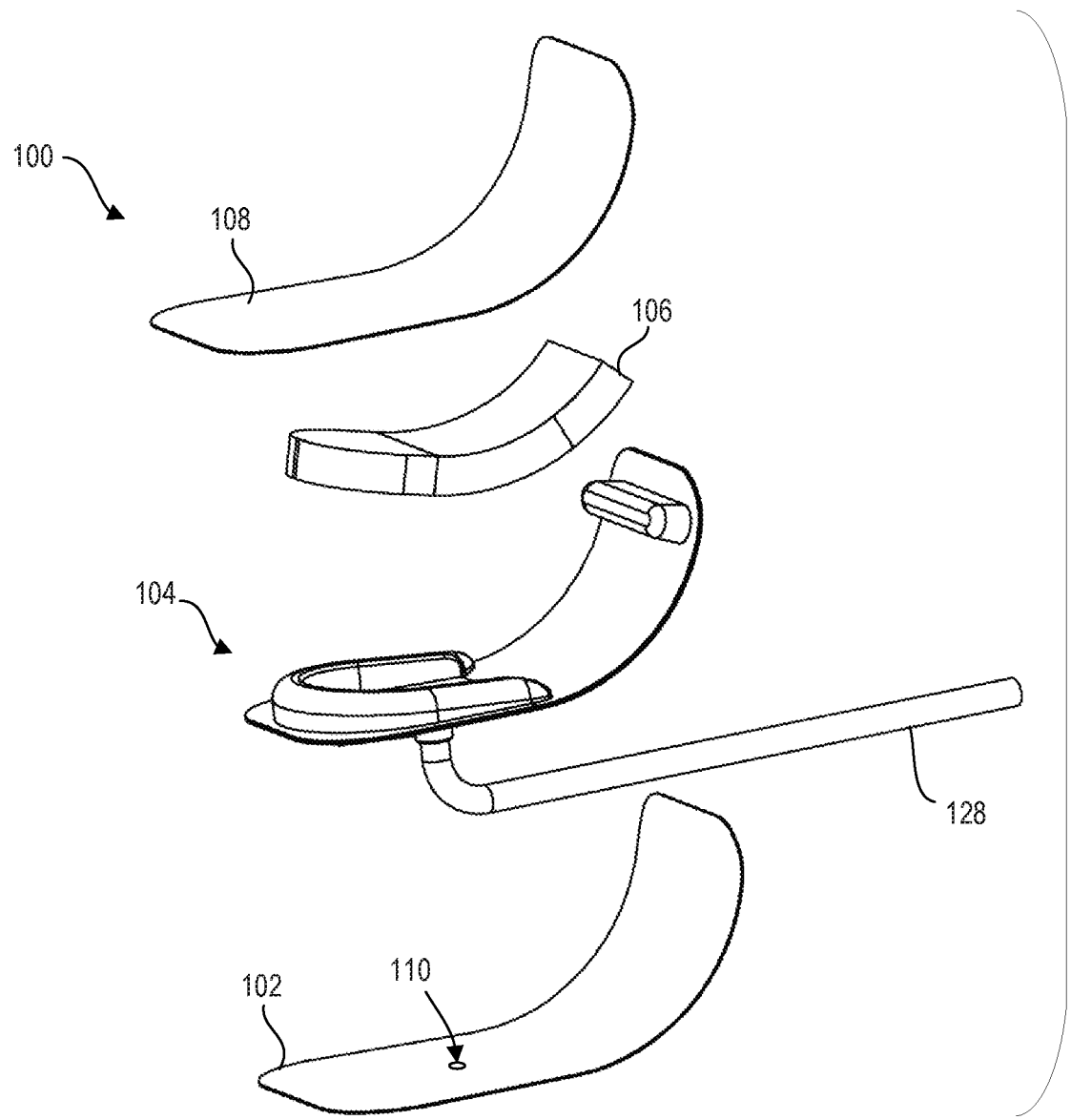
FIG. 28 is an exploded view of the third alternative embodiment of a urinary device.
Figure 29:
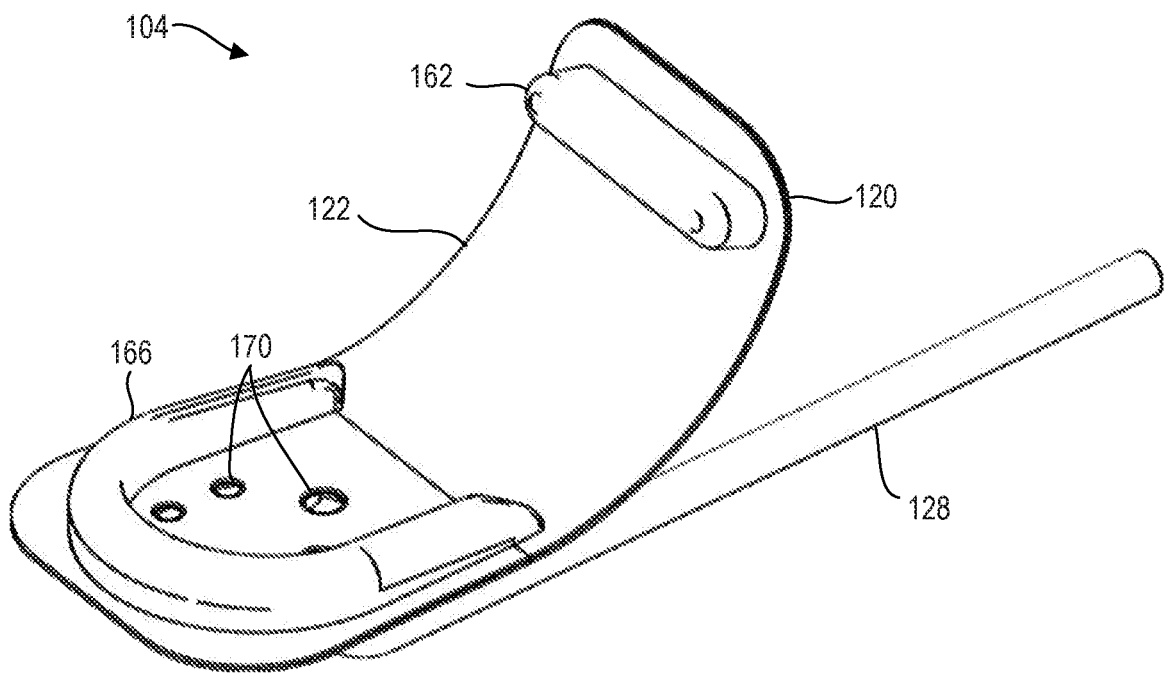
FIG. 29 is a perspective view of a core of the third alternative embodiment of a urinary device.
Figure 30:
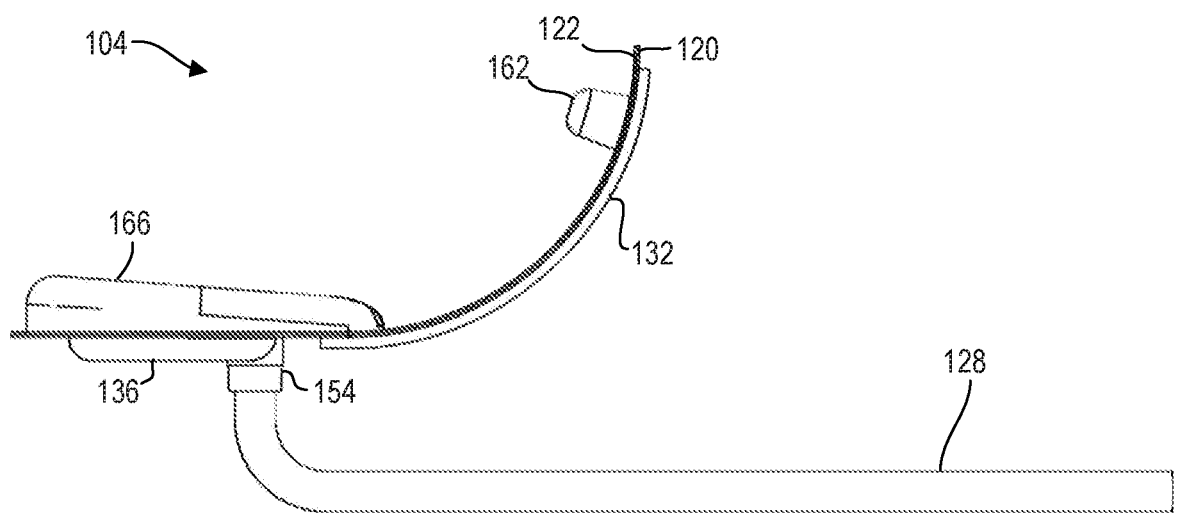
FIG. 30 is a side elevation view of a core of the third alternative embodiment of a urinary device.
Figures 31, 32:
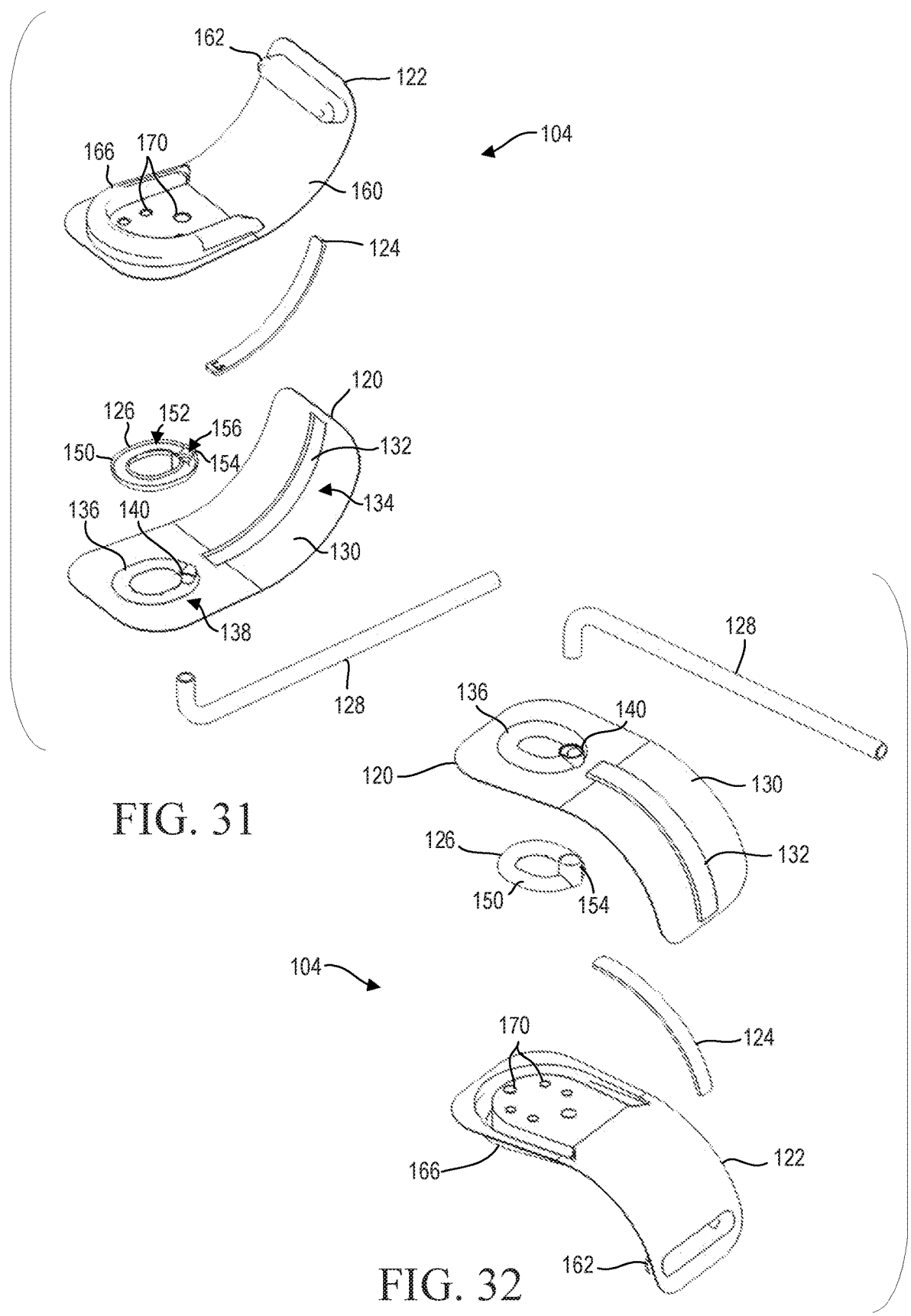
FIG. 31 is an upper exploded view of the core of the third alternative embodiment of a urinary device.
FIG. 32 is a lower exploded view of the core of the third alternative embodiment of a urinary device.
Figure 33:
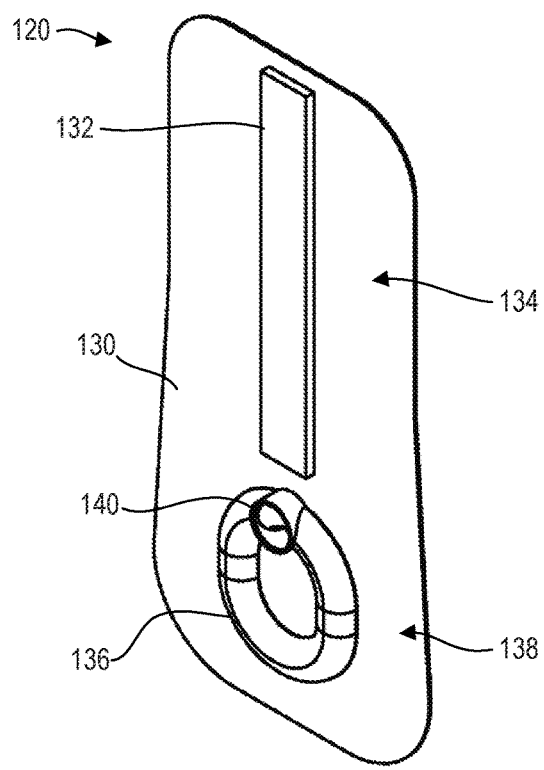
FIG. 33 is a perspective view of a core bottom of the core of the third alternative embodiment of a urinary device.
Figure 34:
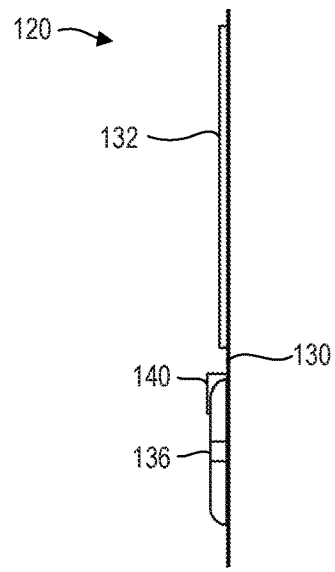
FIG. 34 is a side elevation view of the core bottom of the core of the third alternative embodiment of a urinary device.
Figure 35:
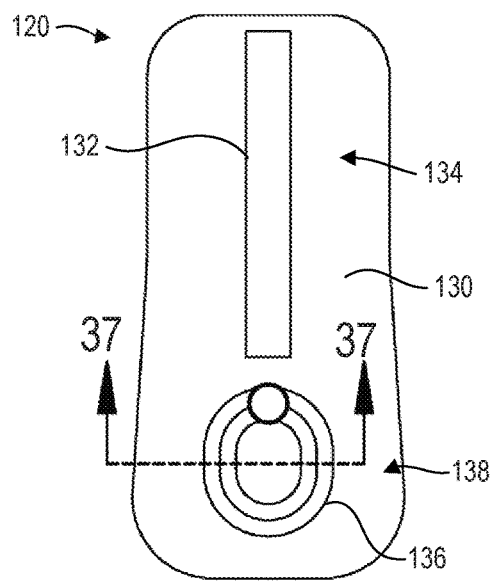
FIG. 35 is a top plan view of the core bottom of the core of the third alternative embodiment of a urinary device.
Figure 36:
FIG. 36 is a front elevation view of the core bottom of the core of the third alternative embodiment of a urinary device.
Figure 37:
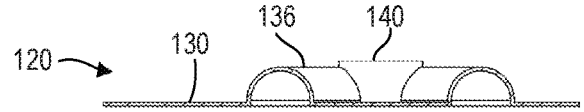
FIG. 37 is a cross-sectional view of the core bottom of the core of the third alternative embodiment of a urinary device taken along the line 37-37 of FIG. 35.
Figure 42:
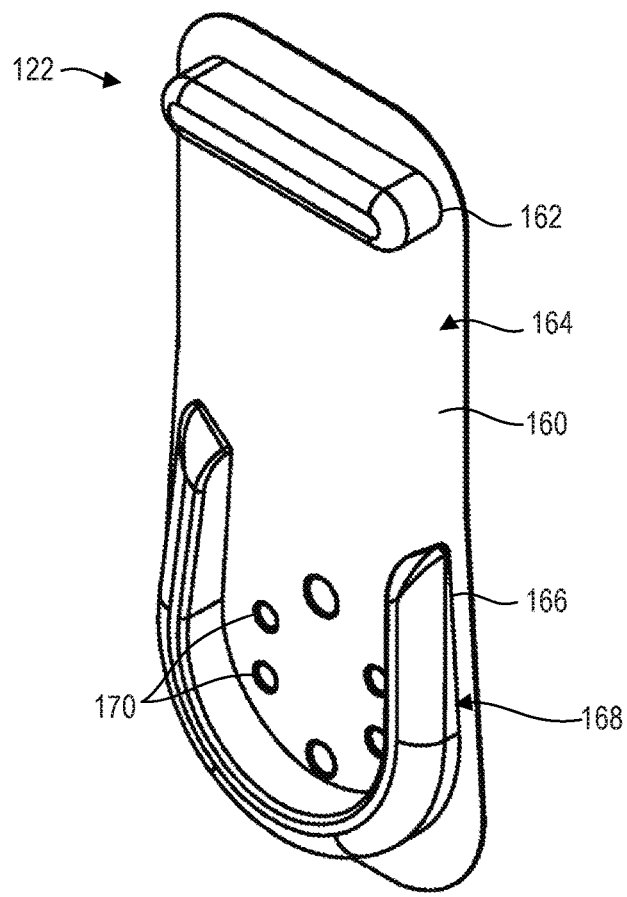
FIG. 42 is a perspective view of a core top of the core of the third alternative embodiment of a urinary device.
Figure 43:
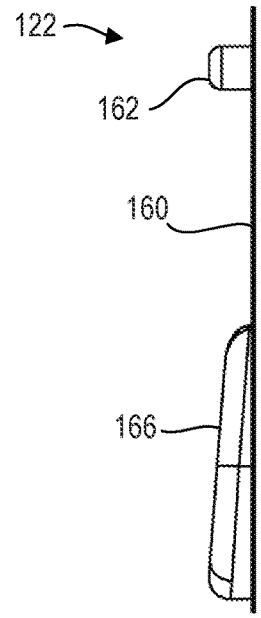
FIG. 43 is a side elevation view of the core top of the core of the third alternative embodiment of a urinary device.
Figure 44:
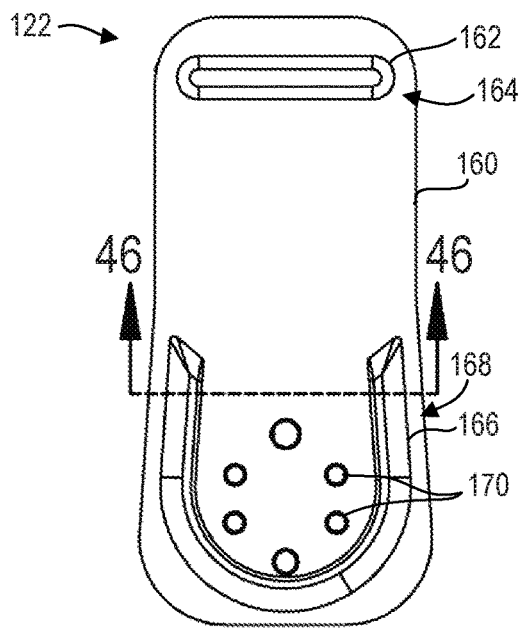
FIG. 44 is a top plan view of the core top of the core of the third alternative embodiment of a urinary device.
Figure 45:
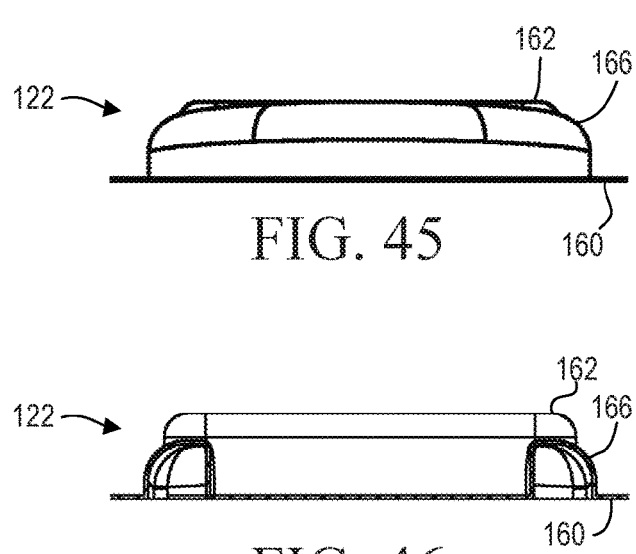
FIG. 45 is a front elevation view of the core top of the core of the third alternative embodiment of a urinary device.
Figure 46:
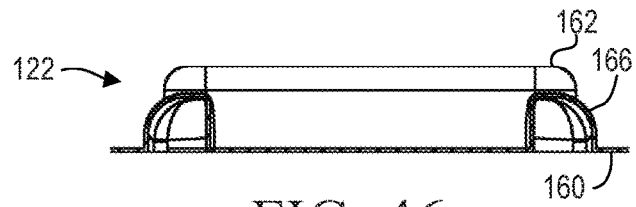
FIG. 46 is a cross-sectional view of the core bottom of the core of the third alternative embodiment of a urinary device taken along the line 46-46 of FIG. 44.

The bottom cover 102 includes a bottom cover tubing aperture 110 disposed therethrough. The bottom cover tubing aperture 110 may extend through the bottom cover 102 to receive an outlet port or tubing therethrough. The bottom cover 102 may be formed of a flexible material such that the bottom cover 102 conforms to the shape of the bottom surface of the core 104, as shown in FIG. 27 in comparison to FIG. 28. More particularly, the bottom cover 102 may be a liquid resistant bottom cover that may be formed of, for example, polyvinyl chloride (PVC), a hydrophobic SMS non-woven material, polyurethane (PU), silicone elastomer, fluoropolymers, or a combination thereof. "Non-woven" refers to materials and webs of material that are formed without the aid of a textile weaving or knitting process. For example, nonwoven materials, fabrics or webs have been formed from many processes such as meltblowing processes, spunbonding processes, air laying processes, and bonded carded web processes.

The liquid transfer layer 106 is disposed between the core 104 and the top cover 108. The liquid transfer layer 106 may be formed, for example, of various polyesters (e.g., fiber fill, vertically aligned, etc.). Other materials for facilitating liquid transfer are expressly contemplated.

The top cover 108 may be a fabric cover that may be formed of, for example, polyester mesh, a polypropylene mesh non-woven material, a polyethylene mesh non-woven material, or a combination thereof. The top cover 108 may be a flexible cover that conforms to the shape of component over which the top cover 108 is disposed (e.g., the liquid transfer layer 106 and the core 104). The top cover 108 may be secured to the bottom cover 102 the maintain the intermediate components in place. The top cover 108 can be sealed to the bottom cover 102 using ultrasonic welding, RF welding, and adhesive to name a few.

Referring to FIGS. 29-32, the core 104 includes a lower core layer, referred to herein as a core bottom 120, and an upper core layer, referred to herein as a core top 122. The core bottom 120 and the core top 122 may be formed, for example, of polyethylene terephthalate (PET).

The core 104 further includes a core center 124 and a connector, also referred to as collector 126, disposed between the core bottom 120 and the core top 122. The core center 124 may be formed of polyethylene terephthalate (PET) and may have a rigidity sufficient to maintain the core 104 in a curved configuration. As will be appreciated, the curved configuration promotes fluid transfer through the core 104. Furthermore, the core center 124 may inhibit straightening of the core 104 (and thereby the urinary device 100), which may contribute to leakage from the urinary device 100.

The core 104 further includes a tubing 128 that extends through the core bottom 120 and into engagement with the collector 126. In one approach, the tubing 128 has an outer diameter of approximately 7.2 millimeters, and an inner diameter of approximately 5.5 millimeters. The tubing 128 may be a flexible tubing such that the tubing 128 may be bendable, as shown in FIGS. 29-32. For example, the tubing 218 may be formed of polyvinyl chloride (PVC).

The core bottom 120, also depicted in FIGS. 33-37, includes a core bottom body portion 130, a core bottom channel 132 that extends away from the core bottom body portion 130 at a first region 134 of the core bottom body portion 130, and a core bottom receptacle portion 136 that extends away from the core bottom body portion 130 at a second region 138 of the core bottom body portion 130. The core bottom channel 132 may be sized and configured to receive the core center 124 therein. The core center 124 may have a thickness, for example, of approximately 1.5 millimeters, and a width of approximately eight millimeters. The core bottom receptacle portion 136 may be sized and configured to receive the collector 126 therein.

The core bottom 120 further includes a core bottom tubing aperture 140 disposed therethrough. The core bottom tubing aperture 140 may extend through the core bottom 120 at the core bottom receptacle portion 136. The core bottom tubing aperture 140 may be sized and configured to receive the tubing 128 therethrough.

The collector 126, also depicted in FIGS. 38-41, includes a channel body 150 that forms a fluid channel 152, which may be in the form of a reservoir. The collector 126 further includes an outlet 154 that extends from the channel body 150 and that forms a fluid outlet 156 that is in fluidic communication with the fluid channel 152. As shown, the channel body 150 may generally be in the form of an oblong channel body. Other shapes and geometries (e.g., annular, circular, oval, etc.) are expressly contemplated. The channel body 150 may extend approximately 37 millimeters along a major axis, and approximately 31 millimeters along a minor axis. The channel body 150 may have a wall of approximately one millimeter in thickness. In one approach, the channel body 150 has an inner dimension, which may correspond to a width of the fluid channel 152, of approximately 7.6 millimeters. The collector 126 may be formed, for example, of polyvinyl chloride (PVC).

The fluid outlet 156 may extend approximately five millimeters from a lower surface of the channel body 150, and may have an inner diameter of approximately 8 millimeters. The fluid outlet 156 may be configured to form a fluid-tight seal, or substantially fluid-tight seal, with the tubing 128. The tubing 128 may be joined to the fluid outlet 156, for example, through chemical bonding (cyclohexanone) or a liquid adhesive. In another approach, the tubing 128 is secured to the fluid outlet 156 via an interference-fit (e.g., press-fit) interface. In still another approach, the tubing 128 is secured to the collector outlet 156 via a threaded interface.

The core top 122, also depicted in FIGS. 42-46, includes a core top body portion 160, and an upper protrusion 162 that extends away from the core top body portion 160 at a first region 164 of the core top body portion 160. The upper protrusion 162 may be a generally oblong protrusion that extends transverse to a major axis of the core top body portion 160. The upper protrusion 162 may assist in maintaining proper alignment of the urinary device 100 and/or may inhibit fluid leakage when the urinary device assembly 30 is secured to a patient 31.

The core top 122 further includes a guide protrusion 166 that extends away from the core top body portion 160 at a second region 168 of the core bottom body portion 160. In the approach shown, the guide protrusion 166 is a generally-U-shaped guide protrusion. In other approaches, the guide protrusion may take the form of other shapes (e.g., V-shaped, funnel shaped, etc.).

The core top 122 may further include one or more apertures 170 disposed through the second region 168 of the core top body portion 160. For example, the core top 122 may include a plurality (e.g., five) annularly spaced apertures 170. The apertures 170 may be provided between a central and side portions of the guide protrusion 166.

In the assembled configuration of the core 104, the core center 124 is received within the core bottom channel 132 of the core bottom body portion 130 of the core bottom 120. The collector 126 is received within the core bottom receptacle portion 136 of the core bottom body portion 130. The core top 122 is disposed over the core center 124, the collector 126, and the core bottom body portion 130. In one approach, in the assembled configuration, the apertures 170 of the core top 122 are aligned, or substantially with the fluid channel 152 of the collector 126 such that fluid (e.g., urine) received at the apertures 170 (e.g., from the liquid transfer layer 106) is directed to the collector 126. From the collector 126, fluid is directed through the outlet 154 of the collector 126 and to the tubing 128 that is connected to the collector 126. The tubing 128, which may correspond to canister suction tube 38 of FIG. 1, may direct the fluid to the canister 37 of FIG. 1.

In the assembled configuration of the urinary device 100, the liquid transfer layer 106 extends along an upper surface of the core 104 (e.g., an upper surface of the core top body portion 160) between the upper protrusion 162 and the guide protrusion 166. At least a portion of the liquid transfer layer 106 extends across the apertures 170 of the core top body portion 160 such that fluid received at the liquid transfer layer 106 is transferred through the apertures and to the collector 126. The curvature of the urinary device 100, as promoted by the core center 124, facilitates flow of the fluid in a direction of the apertures 170 (and thereby the collector 126).

A constricted volume, such as the one created by the core top body portion 160 and the collector 126, is desirable to maintain the negative pressure required to pull fluid from the core 104. In contrast, a fully open collection area, or a collection area having too large of a volume, would require increased suction that may be undesirably or unachievably high in order to carry the fluid away from the urinary device 100. The number of apertures 170, the total aperture area, or both may also be selected to facilitate fluid transfer under a desirable suction. The liquid transfer layer 106 may also act as both a fluid carrier and a surface area restrictor to facilitate fluid transfer under a desirable suction.

All methods described herein can be performed in any suitable order unless otherwise indicated herein or otherwise clearly contradicted by context. The use of any and all examples, or language describing an example (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A urinary device assembly including:
an upper core layer including a body portion and an array of apertures disposed through the body portion, the upper core layer having a guide that at least partially extends from an upper surface of the upper core about the array of apertures,
a lower core layer disposed in at least partial engagement with the upper core layer, and
a collector body insert disposed between the upper core layer and the lower core layer in at least partial alignment with the array of apertures, the collector body insert including a body structure separate from the upper core layer and the lower core layer, the body structure forming a closed-loop U-shaped collector channel having continuous closed inner and outer walls that extend continuously about the body structure on opposite sides of individual apertures of the array of apertures, the inner and outer walls engaging a lower surface of the upper core about the collector body insert, the continuous closed inner lateral loop wall forming a central opening of the collector body insert therebetween that extends through the collector body insert; and
a tube secured to the collector body insert to direct fluid away from the collector body insert.

2. The urinary device assembly of claim 1, further comprising:
a lower cover layer that extends along a lower surface of the lower core layer and in engagement with the collector body insert, the lower cover layer including an aperture for receiving at least a portion of the collector body insert or at least a portion of the tube therethrough; and
a core center disposed between the lower cover layer and the lower core layer, the core center having a rigidity greater than the lower cover layer and the lower core layer, the core center having a radius of curvature that imparts a curvature to the lower cover layer and the lower core layer.

3. The urinary device assembly of claim 1 wherein the collector body insert includes an arcuate channel body and an outlet that protrudes away from the arcuate channel body from a floor portion of the arcuate channel body.

4. The urinary device assembly of claim 1 wherein the collector body insert includes a polyvinyl chloride (PVC) body portion forming a channel and a PVC outlet that extends from the PVC body portion in fluid communication with body portion.

5. The urinary device assembly of claim 1 further comprising:
a lower cover layer that extends along a lower surface of the lower core layer and is formed of a liquid-resistant material, the lower cover layer having a single aperture extending therethrough and in coaxial alignment with the tube and an outlet of the collector body insert.

6. The urinary device assembly of claim 1 further comprising:
a core center having a rigidity greater than the lower core layer, the core center having a radius of curvature that arcs away from the array of apertures to impart a curvature to the lower core layer and the upper core layer that extends away from the array of apertures.

7. The urinary device assembly of claim 1 further comprising:
a liquid transfer layer disposed along the upper core layer and extending over at least a portion of the array of apertures, the liquid transfer layer having an arcuate wall for being received in an arcuate portion of the guide of the upper core layer.

8. The urinary device assembly of claim 1 wherein the collector body insert forms a closed-loop channel and an outlet from the closed-loop channel.

9. The urinary device assembly of claim 1 wherein the collector body insert includes an inner wall and an outer wall extending about the inner wall for receiving fluid therebetween.

10. The urinary device assembly of claim 1 wherein the collector body insert includes a continuous inner wall and a gap between inner wall portions of the continuous inner wall.

11. The urinary device assembly of claim 1 further comprising:
an arcuate core center having a rigidity greater than the lower core layer, the arcuate core center extending along a major axis of the lower core layer axially between the collector body insert and a distal end of the lower core layer.

12. The urinary device assembly of claim 1 wherein the upper core layer further includes a protrusion spaced away from the guide such that raised portions of the protrusion are not connected to raised portions of the guide, and that extends from a common surface of the upper core layer, the guide also extending from the common surface.

13. The urinary device assembly of claim 12 wherein the guide is a generally U-shaped guide having terminal ends defining a space therebetween for guiding fluid therebetween such that at least a portion of the upper core layer does not include the guide.

14. The urinary device assembly of claim 12 wherein the protrusion is a generally oblong protrusion that extends transverse to a major axis of the upper core layer.

15. A urinary device assembly comprising:
a core, the core including:
an upper core layer having a guide that at least partially extends about at least one aperture disposed through the upper core layer,
a lower core layer disposed in at least partial engagement with the upper core layer, and
a collector body insert formed of a liquid-impervious material and disposed between the upper core layer and the lower core layer for receiving fluid from the at least one aperture, the collector body insert having channel walls that form a channel that includes an upper inlet region open to the upper core layer, the channel walls including a continuous closed inner lateral loop wall that forms a central opening of the collector body insert therebetween that extends through the collector body insert, the collector body insert further including an outlet that is integrally-formed formed with the channel walls, the integrally-formed outlet having outlet walls that protrude from a floor portion of the collector body insert opposite the upper inlet region;
a tube secured to the collector body insert at the protruding outlet walls to direct fluid away from the collector body insert.

16. A urinary device assembly comprising:
a core including:
an upper core layer having a protruding guide that at least partially extends about at least one aperture disposed through the upper core layer, a lower core layer in at least partial engagement with the upper core layer, and a collector body insert between the upper core layer and the lower core layer having a trough in at least partial alignment with the at least one aperture, the collector body insert forming a closed-loop having continuous closed inner and outer lateral loop walls that form the trough therebetween for receiving and channeling fluid, the continuous closed inner lateral loop walls forming a central opening of the collector body insert therebetween that extends through the collector body insert, the trough including a closed lower surface, the continuous closed inner and outer lateral loop walls, and an open upper interface opposite the closed lower surface in at least partial alignment with the at least one aperture.

\* \* \* \* \*